(12) United States Patent
Tamura

(10) Patent No.: US 10,105,052 B2
(45) Date of Patent: Oct. 23, 2018

(54) OPHTHALMIC IMAGING APPARATUS AND OPHTHALMIC INFORMATION PROCESSING APPARATUS

(71) Applicant: KABUSHIKI KAISHA TOPCON, Itabashi-ku (JP)

(72) Inventor: Takaichi Tamura, Fujimino (JP)

(73) Assignee: KAUBSHIKI KAISHA TOPCON, Itabashi-ku (JP)

( * ) Notice: Subject to any disclaimer, the term of this patent is extended or adjusted under 35 U.S.C. 154(b) by 0 days.

(21) Appl. No.: 15/509,384

(22) PCT Filed: Aug. 28, 2015

(86) PCT No.: PCT/JP2015/074490
§ 371 (c)(1),
(2) Date: Mar. 7, 2017

(87) PCT Pub. No.: WO2016/039187
PCT Pub. Date: Mar. 17, 2016

(65) Prior Publication Data
US 2017/0273558 A1    Sep. 28, 2017

(30) Foreign Application Priority Data

Sep. 8, 2014  (JP) .................................. 2014-182666

(51) Int. Cl.
*A61B 3/14*    (2006.01)
*A61B 3/10*    (2006.01)
(Continued)

(52) U.S. Cl.
CPC ................ *A61B 3/14* (2013.01); *A61B 3/102* (2013.01); *A61B 3/107* (2013.01); *A61B 3/12* (2013.01)

(58) Field of Classification Search
CPC ........... A61B 3/14; A61B 3/0025; A61B 3/12; A61B 3/102; A61B 3/0058
(Continued)

(56) References Cited

U.S. PATENT DOCUMENTS

| | | | |
|---|---|---|---|
| 2003/0053025 A1 | 3/2003 | Turner et al. | |
| 2011/0090457 A1* | 4/2011 | Shikaumi | A61B 3/14 351/206 |

(Continued)

FOREIGN PATENT DOCUMENTS

| | | |
|---|---|---|
| JP | 2005-516641 A | 6/2005 |
| JP | 2012-75640 A | 4/2012 |
| JP | 2013-94410 | 5/2013 |

OTHER PUBLICATIONS

International Search Report dated Nov. 24, 2015 in PCT/JP2015/074490 filed Aug. 28, 2015.
(Continued)

*Primary Examiner* — Mohammed Hasan
(74) *Attorney, Agent, or Firm* — Oblon, McClelland, Maier & Neustadt, L.L.P.

(57) ABSTRACT

An ophthalmic imaging apparatus of an embodiment includes a measurement unit, an eye model generation unit, and a simulation execution unit. The measurement unit is configured to acquire a data set by applying optical coherence tomography to a three-dimensional region of a subject's eye including an area extending from an anterior surface of a cornea to a surface of a retina. The eye model generation unit is configured to acquire values of one or more parameters of the subject's eye by analyzing the data set acquired by the measurement unit, and to generate a three-dimensional eye model based on the values acquired. The simulation execution unit executes a simulation based on the three-dimensional eye model generated by the eye model generation unit.

2 Claims, 14 Drawing Sheets

(51) Int. Cl.
 *A61B 3/12* (2006.01)
 *A61B 3/107* (2006.01)
(58) Field of Classification Search
 USPC .................................................. 351/200–246
 See application file for complete search history.

(56) References Cited

U.S. PATENT DOCUMENTS

| | | | |
|---|---|---|---|
| 2012/0083667 A1 | 4/2012 | Isogai et al. | |
| 2012/0154746 A1* | 6/2012 | Nozato ................ | A61B 3/1015 351/205 |
| 2014/0104618 A1 | 4/2014 | Potsaid et al. | |
| 2015/0042952 A1* | 2/2015 | Uchida .................. | A61B 3/102 351/206 |
| 2015/0327762 A1 | 11/2015 | Isogai et al. | |

OTHER PUBLICATIONS

Office Action dated Jun. 26, 2018 in Japanese Application No. 2014-182666 filed Sep. 8, 2014 (w/English translation).
Nobuyuki Shoji, "Wavelength Scanning Optical Coherence Tomograph" (SS-OCT), History of Medicine, Feb. 23, 2008, vol. 224 No. 8, pp. 610-611.

\* cited by examiner

OPHTHALMIC IMAGING APPARATUS AND OPHTHALMIC INFORMATION PROCESSING APPARATUS

FIELD

Embodiments described herein relate generally to an ophthalmic imaging apparatus and an ophthalmic information processing apparatus.

BACKGROUND

In the field of ophthalmology, technologies for generating an eye model (model of a subject's eye) are known. For example, Patent Document 1 discloses a technology to generate an eye model for the purpose of specification of an appropriate intraocular lens (IOL) for the patient. The technology includes measurement of the shape of the anterior and posterior surfaces of the cornea, measurement of the axial length, measurement of the thickness and position of the crystalline lens, and measurement of the thickness of the cornea. Based on these measured values and an IOL model, the technology creates an eye model for the subject's eye. Here, the parameter of the subject's eye is measured by a known device.

[Patent Document 1] Japanese Unexamined Patent Application Publication (Translation of PCT Application) No. 2005-516641

With a conventional technology such as described above, there is a possibility that an eye model with high accuracy may not be acquired. For example, when the object is a healthy eye, each of the parameters can be measured with a high degree of accuracy. However, an eye with disease or an eye that has received LASIK surgery in the past, unignorable errors could intervene in the measurements of the parameters. As a result, an eye model based thereon also turns out to include errors. It is needless to say that a simulation (for example, selection and design of an IOL, identification of the insertion position of an IOL) using such an eye model is inappropriate. Here, it should be noted that eyes subjected to eye model generation often have disease.

Further, the conventional technology is configured only to measure values of the parameters of the subject's eye, and it is not capable of obtaining the structure of the subject's eye. Therefore, with the conventional technology, it is not possible to determine whether the measurement values correctly reflect the characteristics of the subject's eye. For example, in the measurement of the axial length, which is the distance from the apex of the cornea to the surface of the retina (to the fovea centralis), it is not possible to determine whether one end of the line segment representing axial length is located at the apex of the cornea and the other end is located at the fovea centralis. Thus, in the case where measurement has been performed in a state in which the line of sight is deviated, the measurement values including errors are used for generating an eye model. In addition, as there is no way to find such facts afterwards, the generated eye model cannot be corrected.

Furthermore, the conventional technology generates an eye model based solely on the measurement values of the parameters, and therefore the conventional technology cannot visualize the actual structure of the subject's eye. As a result, in the case of a simulation by the use of such an eye model, a user ends up having to heavily rely on his/her own experience or skills. This means that the amount of labor and time to be endured on the part of the user remains extensive.

SUMMARY

An object of the present invention is to provide a technology capable of easily acquiring an eye model with high reliability and suitably executing a simulation by the use of the eye model acquired.

In one embodiment, an ophthalmic imaging apparatus includes a measurement unit, an eye model generation unit, and a simulation execution unit. The measurement unit is configured to acquire a data set by applying optical coherence tomography to a three-dimensional region of a subject's eye including an area extending from an anterior surface of a cornea to a surface of a retina. The eye model generation unit is configured to acquire values of one or more parameters of the subject's eye by analyzing the data set acquired by the measurement unit, and to generate a three-dimensional eye model based on the values. The simulation execution unit is configured to execute a simulation based on the three-dimensional eye model generated by the eye model generation unit.

In another embodiment, an ophthalmic information processing apparatus includes a reception unit, an eye model generation unit, and a simulation execution unit. The reception unit is configured to receive a data set acquired by applying optical coherence tomography to a three-dimensional region of a subject's eye including an area extending from an anterior surface of a cornea to a surface of a retina. The eye model generation unit is configured to acquire values of one or more parameters of the subject's eye by analyzing the data set received by the reception unit, and to generate a three-dimensional eye model based on the values acquired. The simulation execution unit is configured to execute a simulation based on the three-dimensional eye model generated by the eye model generation unit.

According to the embodiments, it is possible to easily acquire an eye model with high reliability and suitably execute a simulation by the use of the eye model.

DETAILED DESCRIPTIONS

Figure 1:
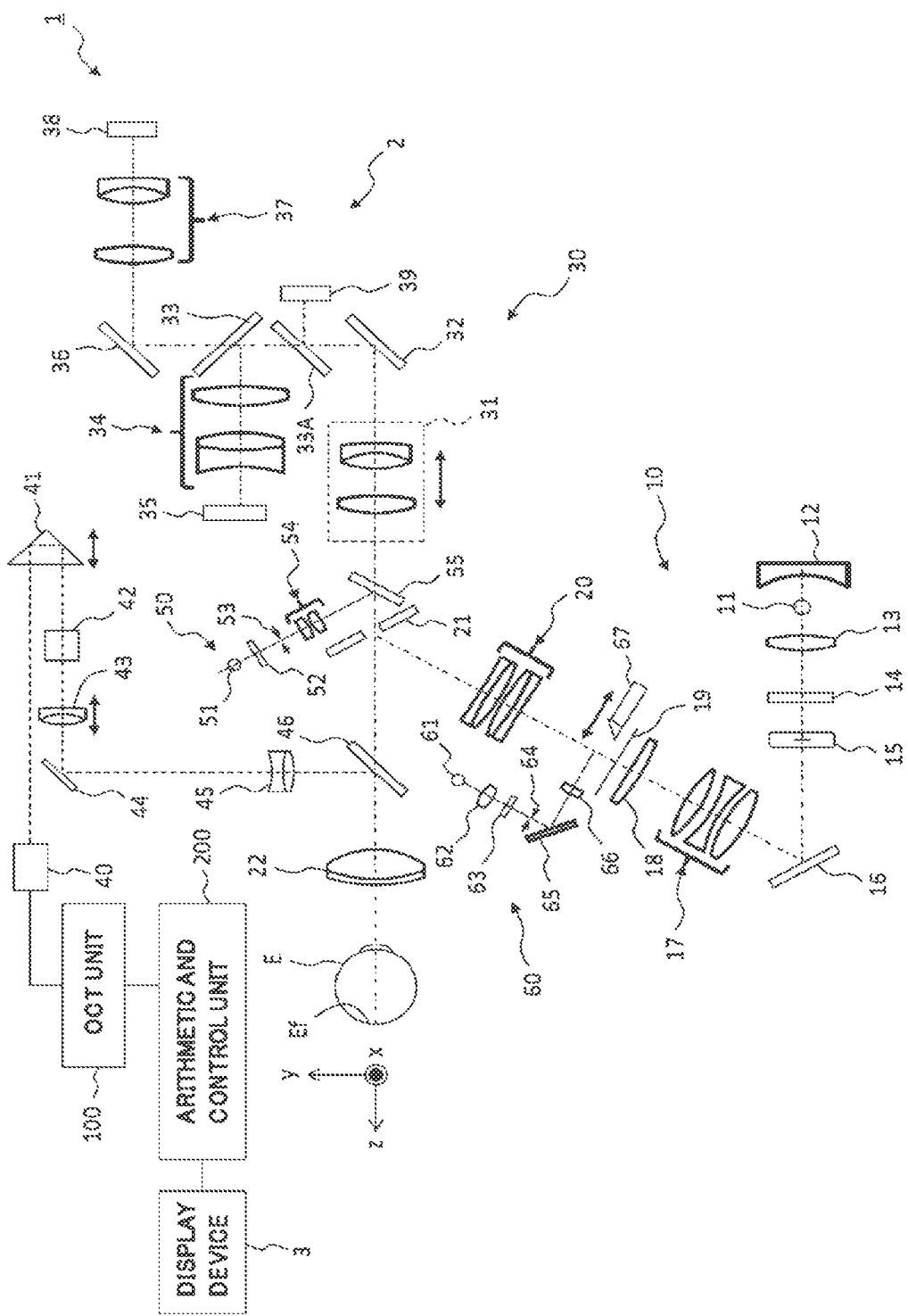
FIG. 1 is a schematic diagram illustrating an example of the configuration of an ophthalmic imaging apparatus according to an embodiment.

Referring now to the drawings, exemplary embodiments of the present invention are described below. An ophthalmic imaging apparatus according to the present invention performs optical coherence tomography (OCT) of a subject's eye. The OCT is applied to at least a three-dimensional region extending from the anterior surface of the cornea of the subject's eye to the surface of the retina. The imaging area by the OCT may include an area between the anterior surface of the cornea and the surface of the retina. The imaging area may be, for example, any one of the followings: an area from the anterior surface of the cornea to an arbitrary position inside the retina; an area from the anterior surface of the cornea to an arbitrary position of the choroid; an area from the anterior surface of the cornea to an arbitrary position of the fundus sclera; and an area from the anterior surface of the cornea to an arbitrary position deeper than the fundus sclera. These are typical examples of the imaging area in the depth direction (i.e., the z direction illustrated in FIG. 1) of the subject's eye. The area in the direction perpendicular to the depth direction (i.e., the x direction and y direction illustrated in FIG. 1) is arbitrary. The imaging area in the xy direction may be set in accordance with, for example, the generation method and/or the purpose (contents of simulation etc.) of the eye model. As a typical example, when an eye model is generated in consideration of the axial length, the imaging area is set so as to include the apex of the cornea and a predetermined region on the surface of the retina (such as the fovea centralis or the center of the retina). As another example, when an eye model is generated in consideration of the shape of the cornea (for example, the curvature or the radius or curvature of the anterior surface of the cornea), the imaging area is set so as to include a predetermined area of the cornea including the apex of the cornea. The predetermined area is, for example, an area required by the algorithm for calculating the curvature).

In the specification, images acquired by using OCT may sometimes be referred to as "OCT images". All the publications referred in the specification may be incorporated in the embodiments described below.

The following embodiment describes an ophthalmic imaging apparatus capable of performing OCT of Fourier domain type. In particular, the ophthalmic imaging apparatus according to the embodiment is capable of applying OCT of swept source type. It should be noted that a configuration according to the embodiment can also be applied to an ophthalmic imaging apparatus capable of performing OCT of a type other than the swept source type such as a spectral domain type. The following embodiment describes an apparatus that is a combination of an OCT apparatus and a fundus camera. However, it is also possible to combine an OCT apparatus having a configuration according to the embodiment with a modality other than the fundus camera. Such a modality may be any of a Scanning Laser Ophthalmoscope (SLO), a slit lamp microscope, an ophthalmic surgical microscope, and the like. Further, a configuration according to the embodiment can be applied to a single-functional OCT apparatus.

First Embodiment

[Configuration]

As shown in FIG. 1, the ophthalmic imaging apparatus 1 includes a fundus camera unit 2, an OCT unit 100, and an arithmetic and control unit 200. The fundus camera unit 2 has substantially the same optical system as a conventional fundus camera. The OCT unit 100 is provided with an optical system for performing OCT. The arithmetic and control unit 200 includes a computer which executes various kinds of arithmetic processing, various kinds of control processing, and the like.

[Fundus Camera Unit]

As illustrated in FIG. 1, the fundus camera unit 2 is provided with an optical system for acquiring two-dimensional images (fundus images) rendering the surface morphology of a fundus Ef of a subject's eye E. Examples of the fundus images include observation images and photographed images. An observation image is, for example, a monochrome moving image with a predetermined frame rate captured using near-infrared light. A photographed image is, for example, a color still image captured by flashing visible light, or a monochrome still image captured using near-infrared light or visible light as illumination light. The fundus camera unit 2 may be configured to be capable of acquiring other types of images such as fluorescein angiograms, indocyanine green angiograms, and autofluorescent angiograms.

The fundus camera unit 2 is provided with a jaw holder and a forehead rest for supporting the face of the subject. Further, the fundus camera unit 2 is provided with an illumination optical system 10 and an imaging optical system 30. The illumination optical system 10 projects illumination light onto the fundus Ef. The imaging optical system 30 guides the illumination light reflected from the fundus Ef to imaging devices (CCD image sensors 35 and 38). Each of the CCD image sensors 35 and 38 is sometimes simply referred to as a "CCD". Further, the imaging optical system 30 guides measurement light coming from the OCT unit 100 to the subject's eye E, and guides the measurement light returning from the subject's eye E to the OCT unit 100.

An observation light source 11 in the illumination optical system 10 includes, for example, a halogen lamp. Light emitted from the observation light source 11 (observation illumination light) is reflected by a reflection mirror 12 having a curved reflective surface, refracted by a condenser lens 13, and becomes near-infrared light after passing through a visible cut filter 14. Further, the observation illumination light is once converged near a flash light source 15, reflected by a mirror 16, and passes through relay lenses 17 and 18, a diaphragm 19, and a relay lens 20. Then, the observation illumination light is reflected on the peripheral part (the surrounding region of an aperture part) of an aperture mirror 21, penetrates a dichroic mirror 46, is refracted by an objective lens 22, and illuminates the fundus Ef. Note that a light emitting diode (LED) may be used as the observation light source 11.

The observation illumination light reflected from the fundus Ef (fundus reflection light) is refracted by the objective lens 22, penetrates the dichroic mirror 46, passes through the aperture part formed in the center region of the aperture mirror 21, passes through a dichroic mirror 55, is refracted by a focusing lens 31, and reflected by a mirror 32. Further, the fundus reflection light passes through a half mirror 33A, is reflected by a dichroic mirror 33, and is converged on the light receiving surface of the CCD image sensor 35 by a condenser lens 34. The CCD image sensor 35 detects the fundus reflection light at a predetermined frame rate, for example. An image (observation image) obtained based on the fundus reflection light detected by the CCD image sensor 35 is displayed on the display device 3. Note that when the focus of the imaging optical system 30 is matched with the anterior segment of the subject's eye E, an observation image of the anterior segment of the subject's eye E is displayed.

The flash light source 15 includes, for example, a xenon lamp. Light emitted from the flash light source 15 (imaging illumination light) is projected onto the fundus Ef via the same route as that of the observation illumination light. Fundus reflection light of the imaging illumination light is guided to the dichroic mirror 33 via the same route as that of the observation illumination light, passes through the dichroic mirror 33, is reflected by a mirror 36, and is converged on the light receiving surface of the CCD image sensor 38 by a condenser lens 37. The display device 3 displays an image (photographed image) obtained based on the fundus reflection light detected by the CCD image sensor 38. Note that the same device or different devices may be used as the display device 3 for displaying the observation image and the display device 3 for displaying the photographed image. Besides, when similar photography is performed by illuminating the subject's eye E with infrared light, an infrared photographed image is displayed. Note that an LED may be used as the flash light source 15.

A liquid crystal display (LCD) 39 displays fixation targets, visual targets for visual acuity tests, etc. A fixation target is an indicator for fixating the subject's eye E, and is used for fundus photography and OCT.

Part of light emitted from the LCD 39 is reflected by the half mirror 33A, is reflected by the mirror 32, travels through the focusing lens 31 and the dichroic mirror 55, passes through the aperture part of the aperture mirror 21, penetrates the dichroic mirror 46, is refracted by the objective lens 22, and is projected onto the fundus Ef.

By changing the position of the fixation target displayed on the screen of the LCD 39, the fixation position can be changed. Examples of the fixation position include, as with conventional fundus cameras, a position for acquiring images centered on the macula of the fundus Ef, a position for acquiring images centered on the optic nerve head, a position for acquiring images centered on the fundus center between the macula and the optic nerve head. Further, the display position of the fixation target may be changed to any desired position.

Further, as with conventional fundus cameras, the fundus camera unit 2 is provided with an alignment optical system 50 and a focus optical system 60. The alignment optical system 50 generates an indicator (alignment indicator) for the registration of the optical system (alignment) with respect to the subject's eye E. The focus optical system 60 generates an indicator (split indicator) for adjusting the focus with respect to the subject's eye E.

Light (alignment light) emitted from an LED 51 in the alignment optical system 50 travels through diaphragms 52 and 53 and a relay lens 54, is reflected by the dichroic mirror 55, passes through the aperture part of the aperture mirror 21, penetrates the dichroic mirror 46, and is projected onto the cornea of the subject's eye E through the objective lens 22.

The alignment light reflected by the cornea (cornea reflection light) travels through the objective lens 22, the dichroic mirror 46 and the aperture part. Part of the cornea reflection light then penetrates the dichroic mirror 55, passes through the focusing lens 31, is reflected by the mirror 32, penetrates the half mirror 33A, is reflected by the dichroic mirror 33, and is projected onto the light receiving surface of the CCD image sensor 35 through the condenser lens 34. The display device 3 displays images (alignment indicator) captured by the CCD image sensor 35 together with the observation image. A user conducts alignment operation in the same way as with the conventional fundus cameras. Alignment may be performed in such a way that the arithmetic and control unit 200 analyzes the position of the alignment indicator and moves the optical system (automatic alignment function).

To conduct focus adjustment, the reflective surface of a reflection rod 67 is placed in a slanted position on the optical path of the illumination optical system 10. Light (focus light) emitted from an LED 61 in the focus optical system 60 passes through a relay lens 62, is split into two light beams by a split indicator plate 63, passes through a two-hole diaphragm 64, is reflected by a mirror 65, is converged on the reflective surface of the reflection rod 67 by a condenser lens 66, and is reflected by the reflection rod 67. Further, the focus light travels through the relay lens 20, is reflected by the aperture mirror 21, penetrates the dichroic mirror 46, is refracted by the objective lens 22, and is projected onto the fundus Ef.

The focus light reflected from the fundus passes through the same route as the cornea reflection light of the alignment light, and is detected by the CCD image sensor 35. The display device 3 displays images (split indicator) captured by the CCD image sensor 35 together with the observation image. As in the conventional fundus cameras, focus adjustment is performed in such a way that the arithmetic and control unit 200 analyzes the position of the split indicator and moves the focusing lens 31 and the focus optical system 60 (automatic focusing function). The user may perform manual focus adjustment operation while observing the split indicator.

The dichroic mirror 46 branches the optical path for OCT from the optical path for fundus photography. The dichroic mirror 46 reflects light of wavelengths used for OCT, and transmits light for fundus photography. The optical path for OCT is formed by, in order from the OCT unit 100 side, a collimator lens unit 40, an optical path length changing unit 41, a variable cross cylinder lens (hereinafter referred to as VCC lens) 47, a galvanometer scanner 42, a focusing lens 43, a mirror 44, and a relay lens 45.

The optical path length changing unit 41 is movable in the direction of the arrows shown in FIG. 1 to change the length of the optical path for OCT. The change in the optical path length is used to correct the optical path length according to the axial length of the subject's eye E, to adjust the interference state, or the like. The optical path length changing unit 41 includes, for example, a corner cube and a mechanism for moving the corner cube.

The galvanometer scanner 42 is arranged in a position optically conjugate with the pupil of the subject's eye E. The galvanometer scanner 42 changes the traveling direction of the light (measurement light LS) passing through the OCT optical path. Thereby, it is possible to scan the subject's eye with the measurement light LS. The galvanometer scanner 42 is configured to include, for example, a galvano mirror which scans the measurement light LS in the x direction, a galvano mirror which scans the measurement light LS in the y direction, and a mechanism that independently drives these galvano mirrors. Thereby, it is possible to deflect the measurement light LS in an arbitrary direction on the xy plane.

[OCT Unit]

Figure 2:
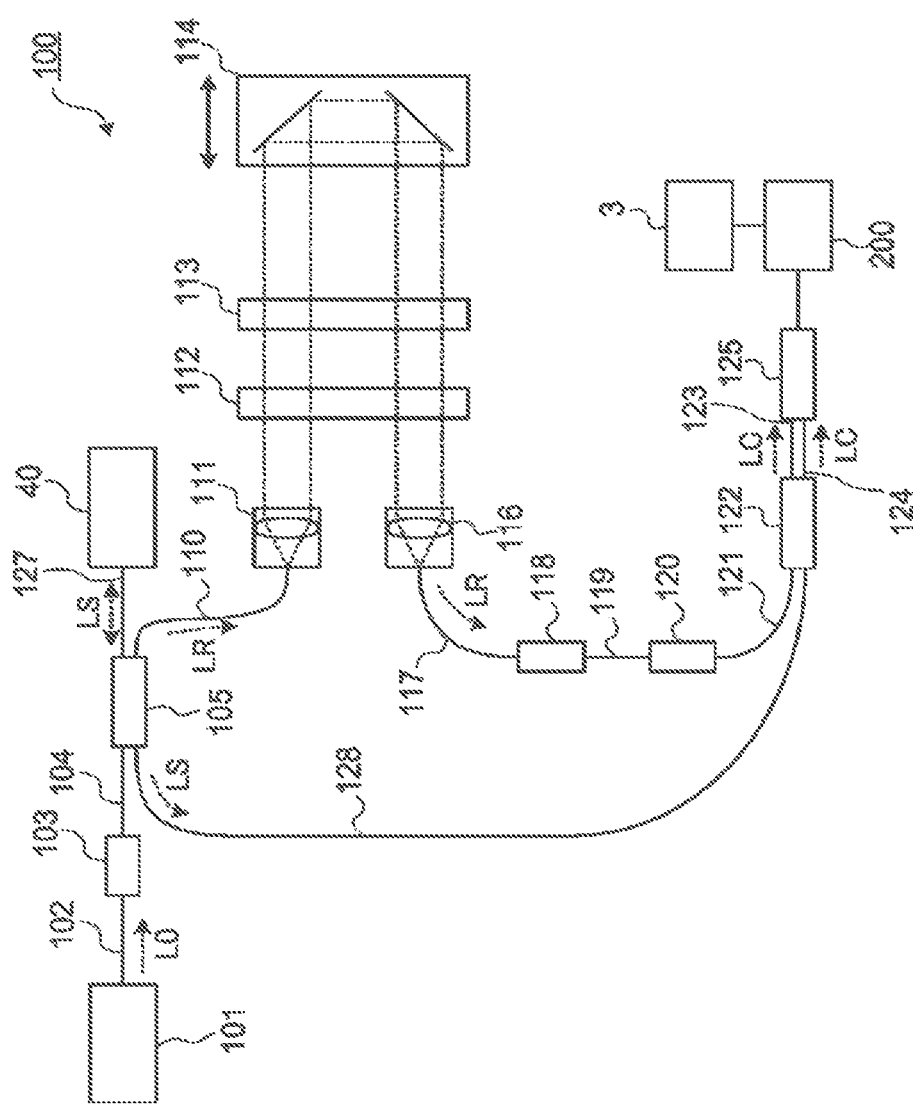
FIG. 2 is a schematic diagram illustrating an example of the configuration of the ophthalmic imaging apparatus according to an embodiment.

An example of the configuration of the OCT unit 100 is shown in FIG. 2. The OCT unit 100 is provided with an optical system for acquiring OCT images of the subject's eye E. The optical system has the same configuration as the conventional OCT apparatuses of swept source type. That is, the optical system is an interference optical system which splits light from a wavelength tunable type (wavelength swept type) light source into measurement light and reference light, generates interference light by superposing the measurement light returning from the subject's eye on the reference light having passed though the reference optical path, and detects the interference light. The detection result (detection signal) of the interference light by the interference optical system is a signal indicating the spectrum of the interference light, and is sent to the arithmetic and control unit 200.

As with the general OCT apparatuses of swept source type, a light source unit 101 includes a wavelength tunable type (wavelength swept type) light source capable of varying (sweeping) the wavelength of emitted light. The light source unit 101 chronologically changes the output wavelength in the near-infrared wavelength band which cannot be visually recognized by the human eye.

The wavelength tunable type light source is, for example, a highly depth reachable light source. The highly depth reachable light source is a light source that outputs light with high depth reachability to the subject's eye E. With the highly depth reachable light source, it is possible to measure a wider depth area at a time in comparison to light sources of other types. The highly depth reachable light source applied in the embodiment has, for example, a characteristic that it can measure at least an area from the anterior surface of the cornea to the retina at a time. A vertical cavity surface emitting laser (VCSEL) is a specific example of the highly depth reachable light source.

In addition to the highly depth reachable light source (first light source), the light source unit 101 may include another wavelength tunable light source (second light source) which has a lower depth reachability than the first light source. The highly depth reachable light source has an advantage of being able to measure a wide depth range at a time, and at the same time has a disadvantage of being unable to achieve high resolution over the whole measurement range. To compensate for such a disadvantage, the light source unit 101 can include, as the second light source, a wavelength tunable light source having a characteristic that the measurement range is relatively narrow and high resolution can be obtained. When the light source unit 101 includes two or more light sources, the two or more light sources are selectively used to perform OCT. The ophthalmic imaging apparatus 1 may also be configured to be able to simultaneously output two or more light beams from two or more light sources with different sweeping wavelengths, and to detect two or more interference light beams separately by separating their optical paths with one or more dichroic mirrors. Incidentally, the ophthalmic imaging apparatus 1 may also be configured to perform the same OCT measurement using a highly depth reachable light source, and to cut out an area with high resolution.

Instead of having the highly depth reachable light source, the light source unit 101 may be provided with a wavelength tunable type light source (second light source) having a lower depth reachability than the highly depth reachable light source. In this case, the ophthalmic imaging apparatus 1 can be configured so that it divides a three-dimensional region, which extends at least from the anterior surface of the cornea to the surface of the retina, into two or more partial regions, and so that it consecutively performs OCT on these partial regions. It should be noted that the two or more partial regions may or may not have overlapping regions. When there are overlapping regions among the two or more partial regions, OCT is consecutively applied to the two or more partial regions of the three-dimensional region, in which the union of the two or more partial regions is the three-dimensional region itself. With such consecutive processes, a group of data sets can be acquired.

Light L0 output from the light source unit 101 is guided to a polarization controller 103 through an optical fiber 102. The polarization controller 103 performs adjustment of polarization state of the light L0. The polarization controller 103 may be configured to adjust the polarization state of the light L0, which is guided inside the optical fiber 102, by externally applying stress to the looped optical fiber 102, for example.

The light L0 whose polarization state is adjusted by the polarization controller 103 is guided to a fiber coupler 105 through an optical fiber 104. The fiber coupler 105 splits the light L0 into measurement light LS and reference light LR.

The reference light LR is guided to a collimator 111 through an optical fiber 110. The collimator 111 converts the reference light LR into a parallel light beam. The reference light LR, which has become a parallel light beam, is guided to a corner cube 114 via an optical path length correction member 112 and a dispersion compensation member 113. The optical path length correction member 112 functions as a delaying means for matching the optical path length (optical distance) of the reference light LR with the optical path length of the measurement light LS. The dispersion compensation member 113 functions as a dispersion compensation means for matching the dispersion characteristics between the reference light LR and the measurement light LS.

The corner cube 114 reverses the traveling direction of the reference light LR that has become a parallel light beam by the collimator 111. The optical path of the reference light LR incident on the corner cube 114, and the optical path of the reference light LR emitted from the corner cube 114 are parallel to each other. Further, the corner cube 114 is movable in a direction along the incident optical path of the reference light LR and the emitting optical path of the same. Through this movement, the length of the optical path of the reference light LR changes.

In the configuration shown in FIG. 1 and FIG. 2, both of the optical path length changing unit 41 and the corner cube 114 with functions as followings are provided but any one of these may be provided instead of both: the optical path length changing unit 41 is for changing the length of the optical path of the measurement light LS (measurement optical path, measurement arm); and the corner cube 114 is for changing the length of the optical path of the reference light LR (reference optical path, reference arm). Other optical members may be employed to change the difference between the measurement optical path length and the reference optical path length.

The reference light LR that has passed through the corner cube 114 travels through the dispersion compensation member 113 and the optical path length correction member 112. Then, the reference light LR is converted from the parallel light beam to a convergent light beam by a collimator 116. Then, the reference light LR enters an optical fiber 117. Then, the reference light LR is guided to a polarization controller 118. Then, the polarization state of the reference light LR is adjusted by the polarization controller 118.

The polarization controller 118 has the same configuration as the polarization controller 103, for example. The reference light LR whose polarization state is adjusted by the polarization controller 118 is guided to an attenuator 120 through an optical fiber 119. The attenuator 120 adjusts the light amount of the reference light LR under the control of the arithmetic and control unit 200. The reference light LR whose light amount is adjusted by the attenuator 120 is guided to a fiber coupler 122 through an optical fiber 121.

Meanwhile, the measurement light LS generated by the fiber coupler 105 is guided through an optical fiber 127, and becomes a parallel light beam by the collimator lens unit 40. The measurement light LS which has become the parallel light beam reaches the dichroic mirror 46 via the optical path length changing unit 41, the galvanometer scanner 42, the focusing lens 43, the mirror 44, and the relay lens 45. Then, the measurement light LS is reflected by the dichroic mirror 46, is refracted by the objective lens 22, and is irradiated onto the subject's eye E. The measurement light LS is scattered (and reflected) at various depth positions of the subject's eye E. The return light of the measurement light LS including such backscattered light travels in the same route as the outward path in the opposite direction, thereby being led to the fiber coupler 105. Then, (the return light of) the measurement light LS reaches the fiber coupler 122 through an optical fiber 128.

The fiber coupler 122 combines (interferes) the measurement light LS incident through the optical fiber 128 and the reference light LR incident through the optical fiber 121 to generate interference light. The fiber coupler 122 generates a pair of interference light LC by splitting the interference light generated from the measurement light LS and the reference light LR at a predetermined splitting ratio (for example, 1:1). The pair of interference lights LC emitted from the fiber coupler 122 is guided to a detector 125 separately through a pair of optical fibers 123 and 124.

The detector 125 is, for example, a balanced photo diode. The balanced photo diode includes a pair of photodetectors for detecting a pair of interference lights LC separately, and outputs the difference between the detection results obtained by the pair of photodetectors. The difference (detection signal) is sent to the arithmetic and control unit 200. For example, the arithmetic and control unit 200 applies Fourier transform and the like to the spectral distribution based on the detection signals obtained by the detector 125 for each series of wavelength sweeping (that is, for each A line), to form the reflection intensity profile in each A line. Further, the arithmetic and control unit 200 applies an imaging process on each A line profile to form image data.

In the embodiment, an interference optical system of Michelson type is employed. However, any type of interference optical system, such as a Mach-Zehnder type, may be employed.

[Arithmetic and Control Unit]

The configuration of the arithmetic and control unit 200 will be described. The arithmetic and control unit 200 analyzes the detection signals input from the detector 125 to form an OCT image of the subject's eye E. The arithmetic processing for the analysis is the same as the conventional swept source type OCT apparatus.

Further, the arithmetic and control unit 200 controls each part of the fundus camera unit 2, the display device 3, and each part of the OCT unit 100. For example, the arithmetic and control unit 200 controls the display device 3 to display an OCT image of the subject's eye E.

As the control of the fundus camera unit 2, the arithmetic and control unit 200 executes controls as followings: control of the operations of the observation light source 11, the flash light source 15 and the LEDs 51 and 61; control of the operation of the LCD 39; control of the movements of the focusing lenses 31 and 43; control of the movement of the reflection rod 67; control of the movement of the focus optical system 60; control of the movement of the optical path length changing unit 41; control of the operation of the galvanometer scanner 42.

As the control of the OCT unit 100, the arithmetic and control unit 200 executes controls as followings: control of the operation of the light source unit 101; control of the movement of the corner cube 114; control of the operation of the detector 125; control of the operation of the attenuator 120; control of the operations of the polarization controllers 103 and 118.

As with conventional computers, the arithmetic and control unit 200 includes a microprocessor, a RAM (Random Access Memory), a ROM (Read Only Memory), a hard disk drive, a communication interface, and the like. A storage device such as the hard disk drive stores a computer program (s) for controlling the ophthalmic imaging apparatus 1. The arithmetic and control unit 200 may include various circuit boards. The circuit boards may include, for example, a circuit board for the formation of OCT images. In addition, the arithmetic and control unit 200 may include an operation device (input device) such as a keyboard and a mouse. Further, the arithmetic and control unit 200 may include a display device such as an LCD.

The fundus camera unit 2, the display device 3, the OCT unit 100, and the arithmetic and control unit 200 may be integrally configured. That is, all of them may be provided within a single housing. Alternatively, they may be distributed in two or more housings.

[Control System]

Figure 3A:
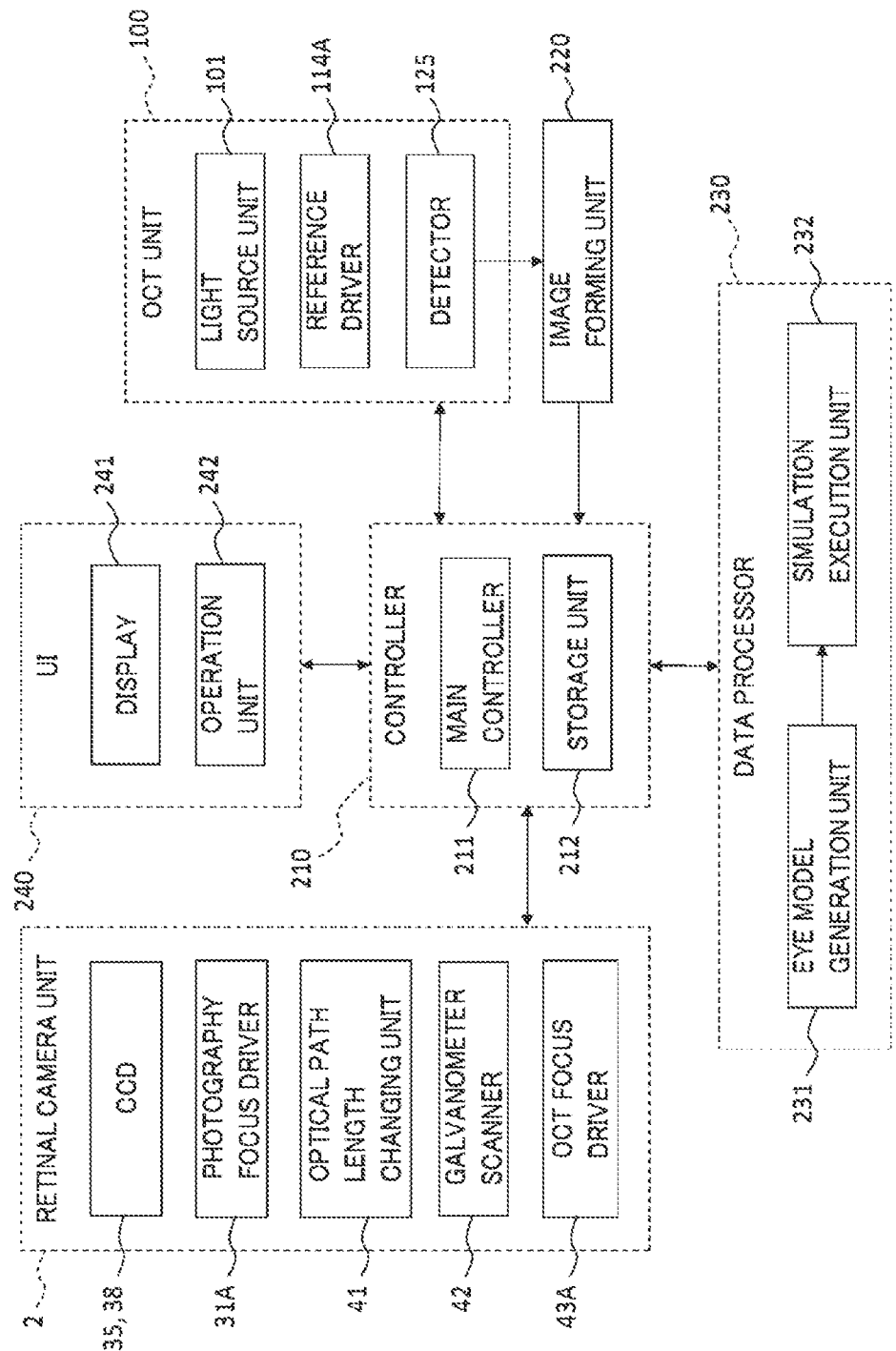
FIG. 3A is a schematic diagram illustrating an example of the configuration of the ophthalmic imaging apparatus according to an embodiment.
Figure 3B:
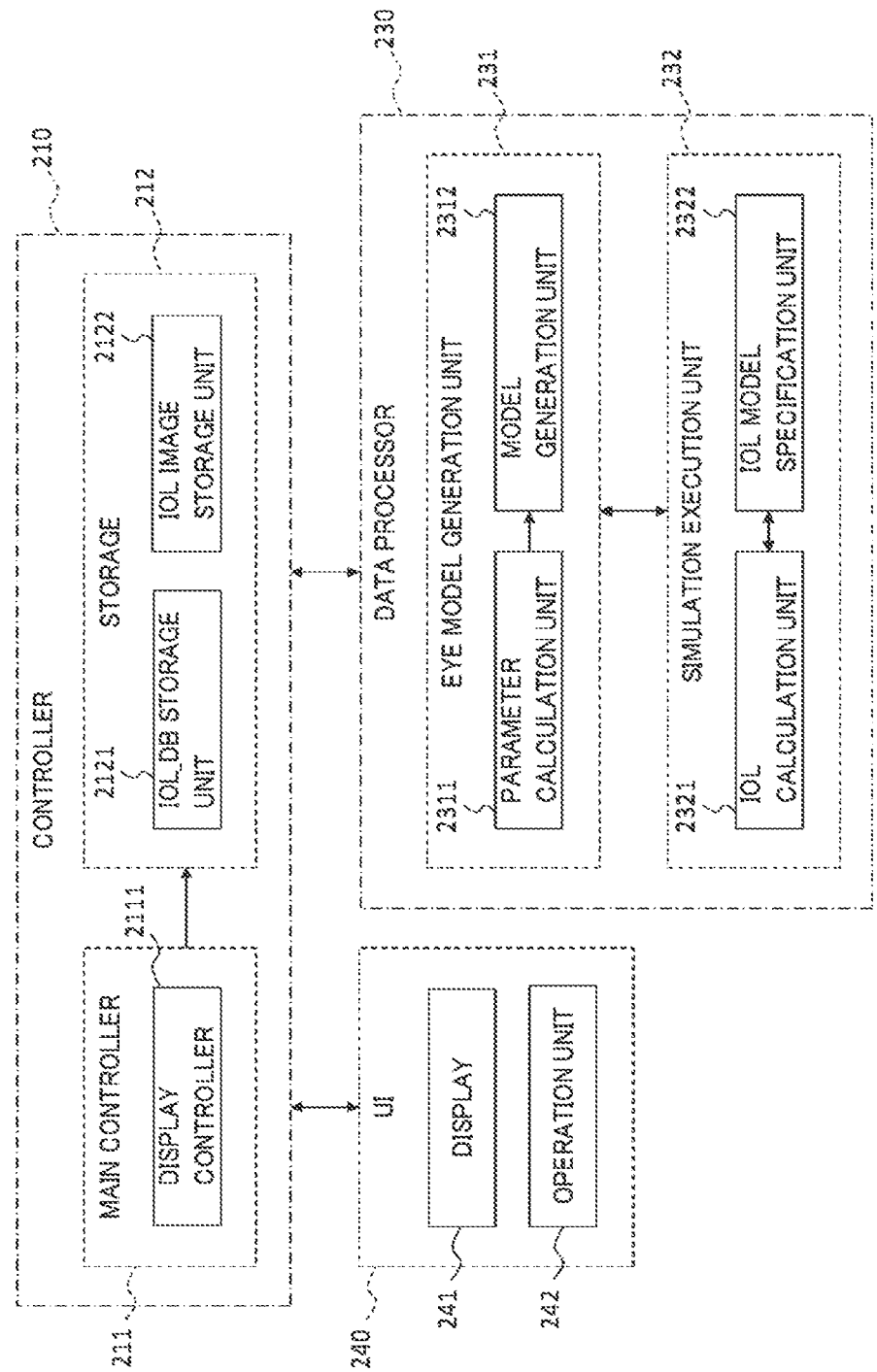
FIG. 3B is a schematic diagram illustrating an example of the configuration of the ophthalmic imaging apparatus according to an embodiment.

The configuration of the control system of the ophthalmic imaging apparatus 1 will be described with reference to FIG. 3A and FIG. 3B. In FIG. 3A and FIG. 3B, some components of the ophthalmic imaging apparatus 1 are omitted. Components which are particularly necessary for describing the present embodiment are selectively shown in FIG. 3A and FIG. 3B.

(Controller)

A controller 210 functions as the center of the control system of the ophthalmic imaging apparatus 1. The controller 210 includes, for example, a microprocessor, a RAM, a ROM, a hard disk drive, a communication interface, and the like. The controller 210 is provided with a main controller 211 and a storage unit 212.

(Main Controller)

The main controller 211 performs the aforementioned various controls. In particular, as shown in FIG. 3A, the main controller 211 controls the following components of the fundus camera unit 2: the CCD image sensors 35 and 38; a photography focus driver 31A; the optical path length changing unit 41; the galvanometer scanner 42; and an OCT focus driver 43A. In addition, as shown in FIG. 3A, the main controller 211 controls the following components of the OCT unit 100: the light source unit 101; a reference driver 114A; and the detector 125.

The photography focus driver 31A is configured to move the focusing lens 31 in the direction along the optical axis. This movement changes the focal position of the imaging optical system 30. Note that the main controller 211 can control an optical system driver (not shown) to three-dimensionally move the optical system provided in the fundus camera unit 2. This control is used in alignment and tracking. Tracking is an operation of moving the optical systems of the apparatus according to the motion of the subject's eye E. When tracking is performed, alignment and focusing are executed in advance. Tracking is performed by moving the optical systems of the apparatus in real time according to the position and direction of the subject's eye E based on a moving image of the eye E. With this, a suitable positional relationship between the optical systems and the eye E, in which the alignment state and the focusing state are appropriate, is maintained.

The OCT focus driver 43A is configured to move the focusing lens 43 along the optical axis of the measurement optical path. This movement changes the focal position of the measurement light LS. The focal position of the measurement light LS corresponds to the depth position (z position) of the beam waist of the measurement light LS.

The reference driver 114A is configured to move the corner cube 114 provided in the reference optical path. This movement changes the length of the reference optical path. As described above, another embodiment may include only the optical path length changing unit 41, while yet another embodiment may include only a combination of the corner cube 114 and the reference driver 114A.

As shown in FIG. 3B, the main controller 211 is provided with a display controller 2111. The display controller 2111 is configured to display various types of information on a display unit 241. The processing executed by the display controller 2111 will be described later.

The main controller 211 writes data in the storage unit 212 and reads data from the storage unit 212.

The controller 210 or the main controller 211 is an example of a "controller" according to the present embodiment.

(Storage Unit)

The storage unit 212 stores various types of data. Examples of the data stored in the storage unit 212 include image data of OCT images, image data of fundus images, and subject's eye information. The subject's eye information includes information related to a subject such as patient ID and name, information related to the subject's eye such as identification information of left eye/right eye, or the like. The storage unit 212 further stores various types of computer programs and data to run the ophthalmic imaging apparatus 1.

As shown in FIG. 3B, the storage unit 212 is provided with an intraocular lens database storage unit (IOL_DB storage unit) 2121 and an intraocular lens image storage unit (IOL image storage unit) 2122.

(Intraocular Lens Database Storage Unit)

In the intraocular lens database storage unit 2121, a database including values of parameters relating to a plurality of intraocular lens models is stored in advance. An intraocular lens model includes, for example, information on the degree (spherical degree, astigmatic degree (cylindrical degree), astigmatic axis, etc.), size, shape, color, and the like of an existing intraocular lens. The types of the intraocular lens models included in the database may be arbitrary. Examples of the types of the intraocular lens models include a single focal (fixed focal) intraocular lens, a multifocal intraocular lens, a toric intraocular lens, a refractive intraocular lens, a diffractive intraocular lens, an adjustable intraocular lens, a multifocal adjustable intraocular lens, a phakic IOL, a hole implantable collamer lens, and the like. In addition to existing intraocular lenses, it is also possible to use an intraocular lens model (custom-made intraocular lens) having a degree obtained by a simulation described later. The database may be appropriately updated with, for example, information on a new type of intraocular lens. This updating process is executed by, for example, a server that manages the running ophthalmic imaging apparatuses via the Internet or a private line.

(Intraocular Lens Image Storage Unit)

In the intraocular lens image storage unit 2122, image data representing intraocular lenses is stored in advance. The image data representing intraocular lenses may include template image data representing a typical shape of an intraocular lens. The image data representing intraocular lenses may include individual image data provided for each type of existing intraocular lens. The image data representing intraocular lenses may include image data provided for each of two or more classifications of intraocular lenses according to the characteristics in shape. Further, the image data representing an intraocular lens may be three-dimensional image data. The image data representing an intraocular lens may be two-dimensional image data representing a shape of the intraocular lens when viewed from a predetermined direction. When the image data representing an intraocular lens is three-dimensional image data, an image representing a view from an arbitrary direction can be obtained by rendering the three-dimensional image data. As for the image data of intraocular lenses, it is possible to apply a similar updating process to the aforementioned database. When the image data is provided for each type or classification of intraocular lenses, it is possible to associate the intraocular lens models (their parameter values) in the intraocular lens database storage unit 2121 and the image data in the intraocular lens image storage unit 2122 in advance.

(Image Forming Unit)

An image forming unit 220 forms image data of a tomographic image of the fundus Ef based on detection signals from the detector 125. That is, the image forming unit 220 forms image data of the subject's eye E based on detection results of the interference light LC obtained by the interference optical system. As with the conventional OCT of swept source type, the image formation processing includes, for example, noise removal (noise reduction), filtering, and Fast Fourier Transform (FFT).

The image data acquired in this manner is a data set including a group of image data. The group of image data is formed by applying an imaging process to the reflection intensity profiles for a plurality of A lines. The A lines correspond to passing routes of the measurement lights LS in the subject's eye E. As an example, a data set acquired by three-dimensional scanning described later is obtained in the present embodiment.

In order to improve the image quality, superposition (or averaging) may be employed. The averaging is synthesis of a plurality of data sets collected by iterative scanning with the same scanning pattern. In the averaging, the plurality of data sets may be regarded as a single data set as a whole.

Alternatively, a combined data set formed by the superposition of the plurality of data sets may be regarded as a single data set.

The image forming unit 220, for example, includes the aforementioned circuit board. In this specification, an "image" created based on image data may be regarded in the same light as the "image data". In addition, an image of a site of the subject's eye E may be regarded in the same light as the site.

(Data Processor)

A data processor 230 performs various types of data processing (image processing) and analysis processing on the OCT image formed by the image forming unit 220. For example, the data processor 230 executes image correction such as luminance correction and dispersion correction. Further, the data processor 230 executes various types of image processing and analysis processing on the image (fundus image, anterior segment image, etc.) obtained by the fundus camera unit 2.

The data processor 230 can form volume data (voxel data) of the subject's eye E by performing known image processing such as interpolation between tomographic images. When displaying an image based on the volume data, the data processor 230 performs rendering processing (volume rendering, MIP (Maximum Intensity Projection), or the like) on the volume data to form a pseudo three-dimensional image viewed from a specific sight line direction.

The data processor 230 can perform position matching (registration) between a fundus image and an OCT image. In the case where a fundus image and an OCT image are acquired in parallel, both of their optical systems are coaxial. Thus, it is possible to perform position matching of a fundus image and an OCT image acquired at the same time (almost at the same time) with reference to the optical axis of the imaging optical system 30. Regardless of the acquisition timings of fundus images and OCT images, it is possible to carry out position matching between a fundus image and an OCT image, by the use of position matching between the fundus image and a front image obtained by projecting at least part of the image area in the OCT image corresponding to the fundus Ef onto the xy plane. Such a position matching method can also be applied even when the optical system for acquiring fundus images and the optical system for acquiring OCT images are not coaxial. Further, even when both optical systems are not coaxial, if the relative positional relationship between these optical systems is known, a position matching method similar to that in the coaxial case can be performed with reference to the relative positional relationship.

As shown in FIG. 3A, the data processor 230 is provided with an eye model generation unit 231 and a simulation execution unit 232.

(Eye Model Generation Unit)

The eye model generation unit 231 is configured to acquire values of parameters related to the subject's eye E by analyzing a data set acquired by OCT Further, the eye model generation unit 231 is configured to generate a three-dimensional eye model of the subject's eye E based on the values of the parameters acquired.

The types of the parameters of the subject's eye E are set in advance. In other words, the contents of the analysis process for obtaining the values of the parameters are determined in advance. The types of the parameters are set, for example, according to the contents of simulation executed in a subsequent stage. In this case, an exemplary configuration may be adopted by which the following processes are performed: preparing table information in which one or more types of parameters are associated with a plurality of options of types of simulations; acquiring a type of parameter corresponding to a type of simulation designated in advance from table information; and obtaining a value for the acquired type of parameter. In another example, it is possible to adopt a configuration of obtaining values for all parameters that can be acquired from analysis of a data set acquired by the OCT.

Typical examples of the types of parameters are size parameters, shape parameters and optical parameters.

A size parameter represents a size of part or whole of an eye. Examples of the size parameter which represents part of the eye include corneal thickness, crystalline lens thickness, anterior chamber depth (distance between the posterior surface of the cornea and the anterior surface of the crystalline lens), retinal thickness, pupil diameter, and the like. Examples of the size parameter which represents the whole of an eye includes axial length.

A shape parameter represents a shape of a site of an eye. The site of the eye may be, for example, the anterior surface of the cornea, the posterior surface of the cornea, the anterior surface of the crystalline lens, the posterior surface of the crystalline lens, the surface of the retina, a predetermined layer of the retina, the choroid, the pupil, the iris, or the like. Further, examples of the parameter which represents the shape include a curvature at a predetermined point, a curvature distribution in a predetermined area, a tilt angle, and the like.

An optical parameter represents an optical function of a site of an eye. Examples of the optical parameters include refractive powers (spherical degree, astigmatic degree, astigmatic axis, etc.) of the cornea (anterior surface thereof, posterior surface thereof), refractive power of the crystalline lens (anterior surface thereof, posterior surface thereof), and the like. The optical parameters may include arbitrary parameters related to aberrations such as chromatic aberration, spherical aberration, comatic aberration, astigmatism, field curvature, distortion, or the like. The optical parameters may include arbitrary parameters related to optical characteristics of a site of an eye, such as refractive index, reflectance, dispersion characteristics, polarization characteristics, or the like.

This embodiment obtains several values of parameters, which are used to select and/or design an intraocular lens, from an OCT data set. Note that some of the values of parameters may be obtained from measurement data other than the OCT data set. The ophthalmic imaging apparatus of the embodiment or an external device acquires such values of parameters. Examples of such types of parameters include a shape of the cornea measured by a keratometer or a corneal topographer, a refractive power obtained by a refractometer, an axial length obtained by an axial length measuring device, and the like. Some of the values of parameters may be acquired from a schematic eye data (such as the Gullstrand's schematic eye). It is also possible to correct a certain value of parameter in the schematic eye data based on the OCT data set or other measurement data, and to apply the corrected value.

The eye model generation unit 231 includes a parameter calculation unit 2311 and a model generation unit 2312 as a configuration for generating an eye model from the OCT data set.

(Parameter Calculation Unit)

The parameter calculation unit 2311 obtains a predetermined value of parameter of the subject's eye E by analyzing an OCT data set. The OCT dataset represent morphology of the three-dimensional region of the subject's eye E including the area extending from the anterior surface of the cornea to the surface of the retina. That is, the three-dimensional region corresponds to the imaging region by the OCT, and the image obtained as the OCT data set renders the morphology of each site of the subject's eye E in the three-dimensional region.

Figure 4:
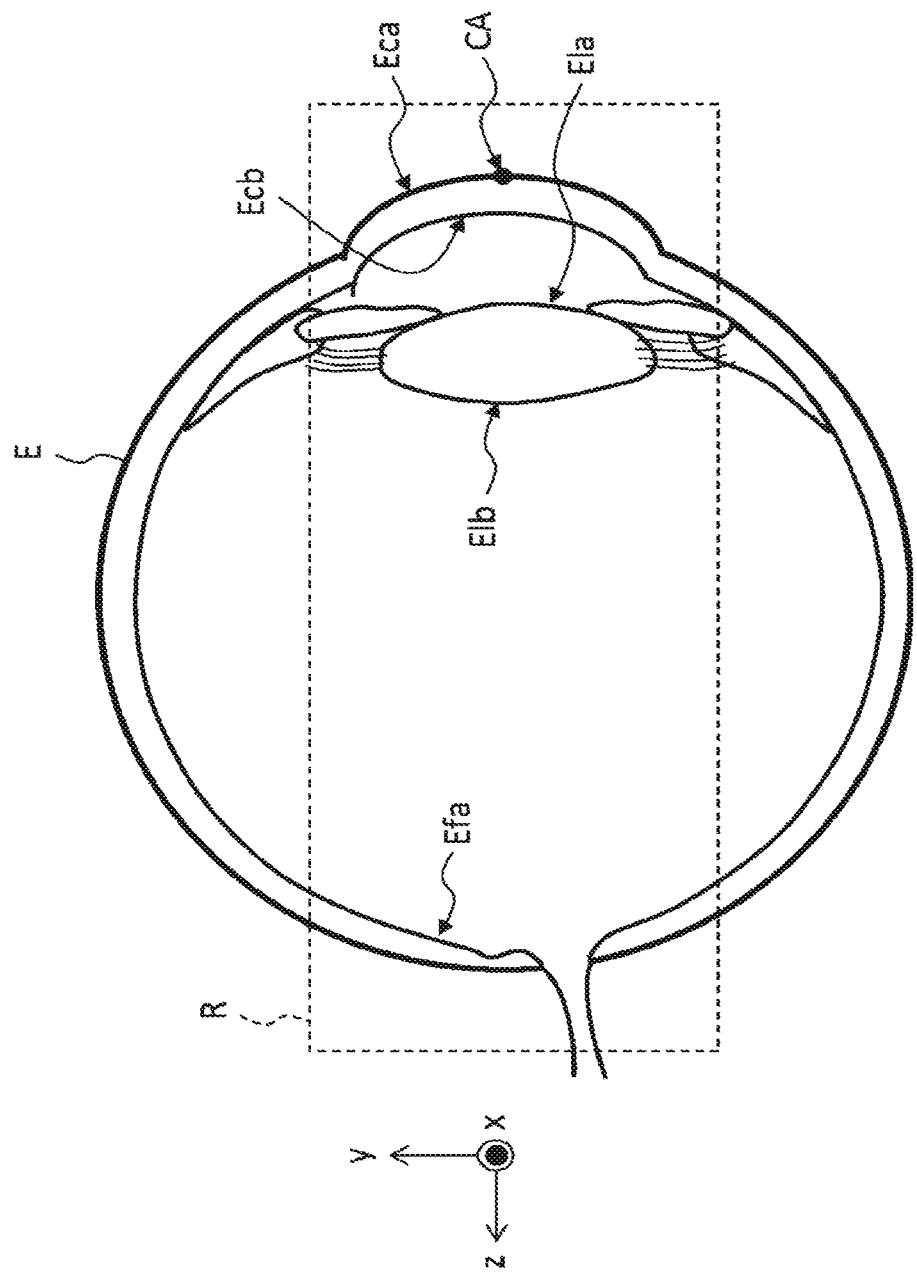
FIG. 4 is a schematic diagram for describing an operation of the ophthalmic imaging apparatus according to an embodiment.

FIG. 4 is a side view of an example of the three-dimensional region. In the z direction, the three-dimensional region R includes an area extending from the anterior surface of the cornea Eca of the subject's eye E to the surface of the retina (surface of the fundus) Efa. Further, in the y direction, the three-dimensional region R extends over a predetermined area. In the x direction, for example, the three-dimensional region R has a width equal to the y direction or a predetermined width different from that of the y direction. The reference symbols used in FIG. 4 are as followings: the reference symbol Eca denotes the anterior surface of the cornea; the reference symbol Ecb denotes the posterior surface of the cornea; the reference symbol CA denotes the apex of the cornea; the reference symbol E1a denotes the anterior surface of the crystalline lens; the reference symbol E1b denotes the posterior surface of the crystalline lens; and the reference symbol Efa denotes the surface of the retina.

An example of the process of calculating a size parameter from the OCT data set will be described. First, the parameter calculation unit 2311 specifies the site of the subject's eye E to be a target of calculation. This processing is executed by analyzing the pixel values of the OCT data set. The processing includes, for example, known image processing such as filtering, threshold processing, edge detection, or the like. Typical examples of the processing include the followings: when obtaining the corneal thickness, the anterior surface of the cornea and the posterior surface of the cornea are specified; when obtaining the crystalline lens thickness, the anterior surface of the crystalline lens and the posterior surface of the crystalline lens are specified; when obtaining then anterior chamber depth, the posterior surface of the cornea and the anterior surface of the crystalline lens are specified; when obtaining the retinal thickness, the anterior surface of the retina and the posterior surface of the retina are specified; when obtaining the pupil diameter, the edge of the iris (i.e., the boundary of the pupil) is specified; and when obtaining then axial length, the anterior surface of the cornea and the surface of the retina are specified.

Next, the parameter calculation unit 2311 specifies two or more feature points in the specified sites. The feature points are used to measure the size. This processing is executed by analyzing the pixel positions and/or the pixel values of the specified site. The processing includes, for example, known image processing such as pattern matching, differential calculation (curvature calculation), filtering, threshold processing, edge detection, or the like. When obtaining the corneal thickness, the apex of the anterior surface of the cornea (the apex of the cornea) and the apex of the posterior surface of the cornea are specified. The apex of the anterior surface of the cornea can be specified, for example, by shape analysis of the anterior surface of the cornea, or can be specified by the z coordinate values of the pixels corresponding to the anterior surface of the cornea. The apex of the posterior surface of the cornea can be specified, for example, as a point of intersection between a straight line passing through the apex of the cornea and extending in the z direction and the posterior surface of the cornea. In another example, the apex of the posterior surface of the cornea can be specified using shape analysis of the posterior surface of the cornea. In yet another example, the apex of the posterior surface of the cornea can be specified by the z coordinate values of the pixels corresponding to the posterior surface of the cornea. Similar processing can be executed for other parameters.

Further, the parameter calculation unit 2311 obtains the size based on the specified two or more feature points. In the case of obtaining the corneal thickness, the distance between the specified apex of the anterior surface of the cornea and the specified apex of the posterior surface of the cornea is calculated. This distance may be represented by, for example, the number of pixels between two apexes, or may be a value obtained by converting the number of pixels into the distance in the real space based on the photographing magnification.

Incidentally, in the case of obtaining the pupil diameter, for example, processing for specifying the center of the pupil is included. Further, it is possible to execute processing of obtaining two intersection points between a line segment passing through the center of the pupil and extending in a predetermined direction (for example, the x direction) and the boundary of the pupil, and to execute processing of calculating the distance between these intersection points as the pupil diameter. As another example, the following processing may be executed: processing of setting a plurality of line segments passing through the center of the pupil and extending in different directions from one another; processing of specifying two intersection points between each of these line segments and the boundary of the pupil; processing of calculating a distance between each pair of the intersections; and processing of obtaining the pupil diameter from the calculated plurality of distances. The last processing may include statistical processing such as maximum value selection processing, average value calculation processing, or the like. It should be noted that similar statistical processing can be executed also in the case of obtaining other parameters.

An example of the processing for calculating a shape parameter from the OCT data set will be described. First, the parameter calculation unit 2311 specifies a target site of the subject's eye E. This processing may be the same as that for the size parameter. Next, the parameter calculation unit 2311 calculates a shape parameter based on the specified site. For example, in the case of obtaining a curvature at a feature point, the feature point can be specified in the same manner as that for the size parameter, and the curvature at this feature point can be calculated based on the shape in the vicinity of the feature point. When obtaining the curvature distribution in a predetermined area, the same processing may be executed for each point within the area. In the case of obtaining the tilt angle, differential processing can be executed based on a concerned position (point) and the shape of a neighborhood region of the position.

An example of processing for calculating an optical parameter from the OCT data set will be described. The OCT data set represents the morphology (shape, size, etc.) of the site of the subject's eye E. With regard to an optical parameter that can be calculated from only the morphology of the site, it is possible to calculate the optical parameter by the use of a known mathematical formula which associates the shape, size, or the like of the site and the optical parameter. With respect to an optical parameter which cannot be calculated from only the morphology of the site, it is possible to calculate the optical parameter by the use of a known mathematical formula with referring to other necessary values (e.g., a measurement value, or a standard value such as schematic eye data, etc.). For example, when obtaining the refractive power of the crystalline lens, it is possible to refer to the refractive index of the crystalline lens and the refractive index of the site adjacent thereto. It is also possible to calculate the refractive power by performing ray tracing under the assumption of paraxial approximation.

(Model Generation Unit)

The model generation unit 2312 generates a three-dimensional eye model of the subject's eye E, based on the value of parameter calculated by the parameter calculation unit 2311. The three-dimensional eye model includes an image (three-dimensional OCT image) expressed by the OCT data sets and the value of parameter calculated by the parameter calculation unit 2311.

For example, as shown in FIG. 4, when the three-dimensional OCT image does not depict the entire subject's eye E, it is possible to complement an image of a non-depicted site to the three-dimensional OCT image. The image of the non-depicted site may be a schematic image or other photographed image (e.g., OCT image, SLO image, anterior segment image, fundus image, ultrasonic image, magnetic resonance imaging (MRI) image, etc.).

The model generation unit 2312 associates each of the values of parameters calculated by the parameter calculation unit 2311 with a corresponding site in the three-dimensional OCT image. This processing is executed, for example, by associating the value of parameter with the site or feature point specified in the process of calculating this value of parameter. For example, the value of parameter representing the shape of the anterior surface of the cornea (e.g., curvature or curvature distribution of the cornea) is associated with the anterior surface of the cornea in the three-dimensional OCT image. Also, the value of parameter representing the axial length of the eye, is associated with both the anterior surface of the cornea (the apex of the cornea, etc.) and the surface of the retina (fovea centralis, etc.) in the three-dimensional OCT image. The same applies to other values of parameters.

(Simulation Execution Unit)

The simulation execution unit 232 executes a simulation based on the three-dimensional eye model generated by the eye model generation unit 231. The simulation in this embodiment is executed to obtain the degree and insertion position of the IOL, but the purpose of simulation is not limited to this. The purpose of simulation and contents corresponding thereto are optional as long as the simulation is executed by the use of an eye model.

The simulation execution unit 232 includes an intraocular lens calculation unit (IOL calculation unit) 2321 and an intraocular lens model specification unit (IOL model specification unit) 2322.

(Intraocular Lens Calculation Unit)

The intraocular lens calculation unit 2321 calculates the degree and the insertion position of the intraocular lens applied to the subject's eye E by executing the simulation based on the three-dimensional eye model. In this case, at least the value of the axial length and the value of the curvature of the anterior surface of the cornea of the subject's eye E are used for generating the three-dimensional eye model. Incidentally, it is possible to generate a three-dimensional eye model by adding a value of parameter other than the aforementioned values of parameters for the purpose of improving the reliability and accuracy of the simulation or according to the type of the IOL. For example, a value of parameter related to the crystalline lens may be added.

The simulation executed by the intraocular lens calculation unit 2321 may include ray tracing for light passing through the three-dimensional eye model. In this embodiment, the three-dimensional eye model used for ray tracing may be any of the followings: the three-dimensional eye model of the subject's eye E generated by the eye model generation unit 231; a three-dimensional eye model obtained by changing characteristics (refractive power, shape, etc.) of a site (crystalline lens, cornea, etc.) of the subject's eye; a three-dimensional eye model obtained by replacing the crystalline lens in the original three-dimensional eye model with an intraocular lens. In the case where an intraocular lens is to be inserted in a state where a crystalline lens is being left as in the case of a phakic IOL, the meaning of "replacing the crystalline lens with an intraocular lens" is defined to include the meaning of "inserting an intraocular lens in a state where a crystalline lens is being left".

Ray tracing is a method of simulating the behavior of light by the use of rays. In this embodiment, the behavior of light passing through the three-dimensional eye model is obtained by using geometrical optics to determine the influence, on the ray, of the cornea, crystalline lens, and the like of the three-dimensional eye model. As a typical example, specular reflection, diffuse reflection or the like is applied to reflection of light, and refraction is calculated by using Snell's law, matrix operation, or the like. Scattering of light may be taken into consideration in ray tracing.

With such ray tracing, it is possible to estimate the aberration that the image of an object projected onto the retina (fundus Ef) of the subject's eye E undergoes. The object may be, for example, a visual target for visual acuity tests such as a Landolt's ring, or may be other patterns.

A typical example of simulation executed by the intraocular lens calculation unit 2321 will be described. First, the intraocular lens calculation unit 2321 executes ray tracing on the assumption that the Landolt's ring is presented to the three-dimensional eye model of the subject's eye E generated by the eye model generation unit 231. Thereby, a retinal projection image of the Landolt's ring, which is affected by the aberration caused by the three-dimensional eye model, is obtained.

Next, the intraocular lens calculation unit 2321 compares the acquired retinal projection image with the presented Landolt's ring (virtual object) or with a predetermined retinal projection image obtained in a state not affected by aberration, thereby calculating an evaluation value representing the difference between them. Further, the intraocular lens calculation unit 2321 determines whether the calculated evaluation value is equal to or less than a predetermined threshold value. When the evaluation value is determined to be equal to or less than the threshold value, which indicates that an intraocular lens need not be applied to the subject's eye E, the intraocular lens calculation unit 2321 sends information indicating the result of the determination to the controller 210.

On the other hand, when the evaluation value is determined to be exceeding the threshold value, the intraocular lens calculation unit 2321 changes the characteristics of the crystalline lens of the subject's eye E (refractive power, position, etc. thereof) based on the evaluation value (and the threshold value) or based on the difference between the retinal projection image and the virtual object presented. Then, the intraocular lens calculation unit 2321 sends the changed value of the characteristic to the eye model generation unit 231. The eye model generation unit 231 generates a new three-dimensional eye model by using the changed value of the characteristic, and sends the new three-dimensional eye model to the simulation execution unit 232.

Based on the new three-dimensional eye model, the intraocular lens calculation unit 2321 again executes the same simulation as described above. Thereby, a retinal projection image of the Landolt's ring which is affected by the aberration caused by the new three-dimensional eye model is obtained. Further, the intraocular lens calculation unit 2321 executes again the same determination processing as above and obtains a new value of the characteristic of the crystalline lens as necessary.

The above series of processes is repeated until the evaluation value is determined to be equal to or less than the threshold value in the determination processing. Thereby, a three-dimensional eye model is acquired in which the refractive power (degree) and position of the crystalline lens are adjusted so as to obtain a suitable retinal projection image. Here, the adjusted degree of the crystalline lens corresponds to the degree of an intraocular lens which is to replace the crystalline lens, and the adjusted position of the crystalline lens corresponds to an insertion position of the intraocular lens.

(Intraocular Lens Model Specification Unit)

As described above, the intraocular lens database storage unit 2121 stores a database including values of parameters of a plurality of intraocular lens models. The intraocular lens model specification unit 2322 specifies an intraocular lens model corresponding to the degree of the intraocular lens (the adjusted degree of the crystalline lens) obtained by the intraocular lens calculation unit 2321 from among the intraocular lens models stored in the database. This processing is performed by comparing the degree of the intraocular lens (the adjusted degree of the crystalline lens) obtained by the intraocular lens calculation unit 2321 with the degrees of the intraocular lens models stored in the database.

When the intraocular lens model specification unit 2322 retrieves an intraocular lens model having a degree equal to the degree of the intraocular lens (the adjusted degree of the crystalline lens), the intraocular lens model specification unit 2322 selects the retrieved intraocular lens model. On the other hand, when the intraocular lens model having a degree equal to the degree of the intraocular lens (the adjusted degree of the crystalline lens) is not found, the intraocular lens model specification unit 2322 may select an intraocular lens model having the degree closest to the degree of the intraocular lens (the adjusted degree of the crystalline lens). Here, the intraocular lens model specification unit 2322 may select an intraocular lens model for a more longsighted eye (alternatively, for a more shortsighted eye) in comparison to the intraocular lens (the adjusted degree of the crystalline lens).

The eye model generation unit 231 can generate a three-dimensional eye model in which the crystalline lens has been replaced with the intraocular lens model specified by the intraocular lens model specification unit 2322. In the three-dimensional eye model, the specified intraocular lens model is arranged at the position of the crystalline lens adjusted by the eye model generation unit 231. Further, the intraocular lens calculation unit 2321 can perform ray tracing using the three-dimensional eye model. With the ray tracing, it is possible to check whether the selected intraocular lens model (and therefore, the intraocular lens corresponding to the intraocular lens model) is suitable for the subject's eye E. When the evaluation value obtained by the ray tracing by the use of the three-dimensional eye model exceeds a predetermined threshold value, the above processing can be executed again until the evaluation value becomes equal to or less than the threshold value.

The data processor 230 functioning as described above includes, for example, a microprocessor, a RAM, a ROM, a hard disk drive, a circuit board, and the like. In a storage device, such as a hard disk drive, computer programs for causing the microprocessor to execute the above functions may be stored in advance.

(User Interface)

A user interface 240 includes the display unit 241 and an operation unit 242. The display unit 241 includes the display device provided in the arithmetic and control unit 200 and/or the display device 3. The operation unit 242 includes the operation devices provided in the arithmetic and control unit 200. The operation unit 242 may include various types of buttons and keys provided on the case of the ophthalmic imaging apparatus 1 or provided outside it. For example, when the fundus camera unit 2 has a case like those of conventional fundus cameras, the operation unit 242 may include a joy stick, an operation panel, and the like provided on the case. Besides, the display unit 241 may include various types of display devices, such as a touch panel, provided on the case of the fundus camera unit 2.

The display unit 241 and the operation unit 242 need not necessarily be formed as separate devices. For example, a device like a touch panel, which has a display function integrated with an operation function, may be employed. In such cases, the operation unit 242 includes the touch panel and computer programs. Contents of operations performed using the operation unit 242 (electrical signals) are fed to the controller 210. Moreover, operations and inputs of information may be performed using a graphical user interface (GUI) displayed on the display unit 241 and the operation unit 242.

[Scanning of Measurement Light and OCT Images]

Here, the scanning of the measurement light LS and OCT images will be described.

Examples of the scanning manner (scanning pattern) of the measurement light LS performed by the ophthalmic imaging apparatus 1 include horizontal scanning, vertical scanning, cross-shaped scanning, radial scanning, circular scanning, concentric circular scanning, spiral (helical) scanning, and the like. These scanning patterns are appropriately and selectively used in consideration of the observation site of the fundus, the analysis target (the form of the lamina cribrosa, etc.), the time required for scanning, the fineness of scanning, and the like.

In the horizontal scanning, the subject's eye E is scanned with the measurement light LS in the horizontal direction (x direction). The horizontal scanning also includes a mode of scanning the subject's eye E with the measurement light LS along a plurality of horizontally extending scanning lines arranged in the vertical direction (y direction). Such a scanning mode is referred to as three-dimensional scanning. In other words, in the three-dimensional scanning, the three-dimensional region of the subject's eye E is scanned. In the three-dimensional scanning, the interval between the scanning lines may be arbitrarily set. With sufficiently narrow interval between adjacent scanning lines, volume data can be formed. The same applies to the vertical scanning.

In the cross-shaped scanning, the subject's eye E is scanned with the measurement light LS along a cross-shaped trajectory composed of two linear trajectories (line trajectories) orthogonal to each other. In the radial scanning, the subject's eye E is scanned with the measurement light LS along a radial trajectory composed of a plurality of linear trajectories arranged at a predetermined angle interval. The cross-shaped scanning is an example of the radial scanning.

In the circular scanning, the subject's eye E is scanned with the measurement light LS along a circular trajectory. In the concentric circular scanning, the subject's eye E is scanned with the measurement light LS along a plurality of circular trajectories arranged concentrically around a predetermined center position. The circular scanning is an example of the concentric circular scanning. In the spiral scanning, the subject's eye E is scanned with the measurement light LS along a spiral (helical) trajectory while gradually decreasing (or increasing) the rotation radius.

Since the galvanometer scanner 42 is configured to deflect the measurement light LS in mutually orthogonal directions, the measurement light LS can be independently deflected in the x direction and the y direction. Furthermore, by simultaneously controlling the orientations of the two galvano mirrors included in the galvanometer scanner 42, the measurement light LS can be deflected along an arbitrary trajectory on the xy plane. With this, various scanning patterns as described above can be implemented.

By performing the scanning with the measurement light LS in the above-described manner, it is possible to acquire a tomographic image corresponding to a cross section spanned by a direction along the scanning line (scanning trajectory) and a depth direction (z direction).

The area of the subject's eye E to be scanned with the measurement light LS as described above, that is, the area of the subject's eye E to which OCT is applied, is called a scanning area. The scanning area in the three-dimensional scanning is a rectangular area in which a plurality of horizontal scanning lines is arranged. The scanning area in the concentric circular scanning is a disk-shaped area defined by the trajectory of the circular scanning of the maximum diameter. The scanning area in the radial scanning is defined by a circle of a polygon formed by connecting the endpoints of the scanning lines.

[Examples of Operation]

Figure 5:
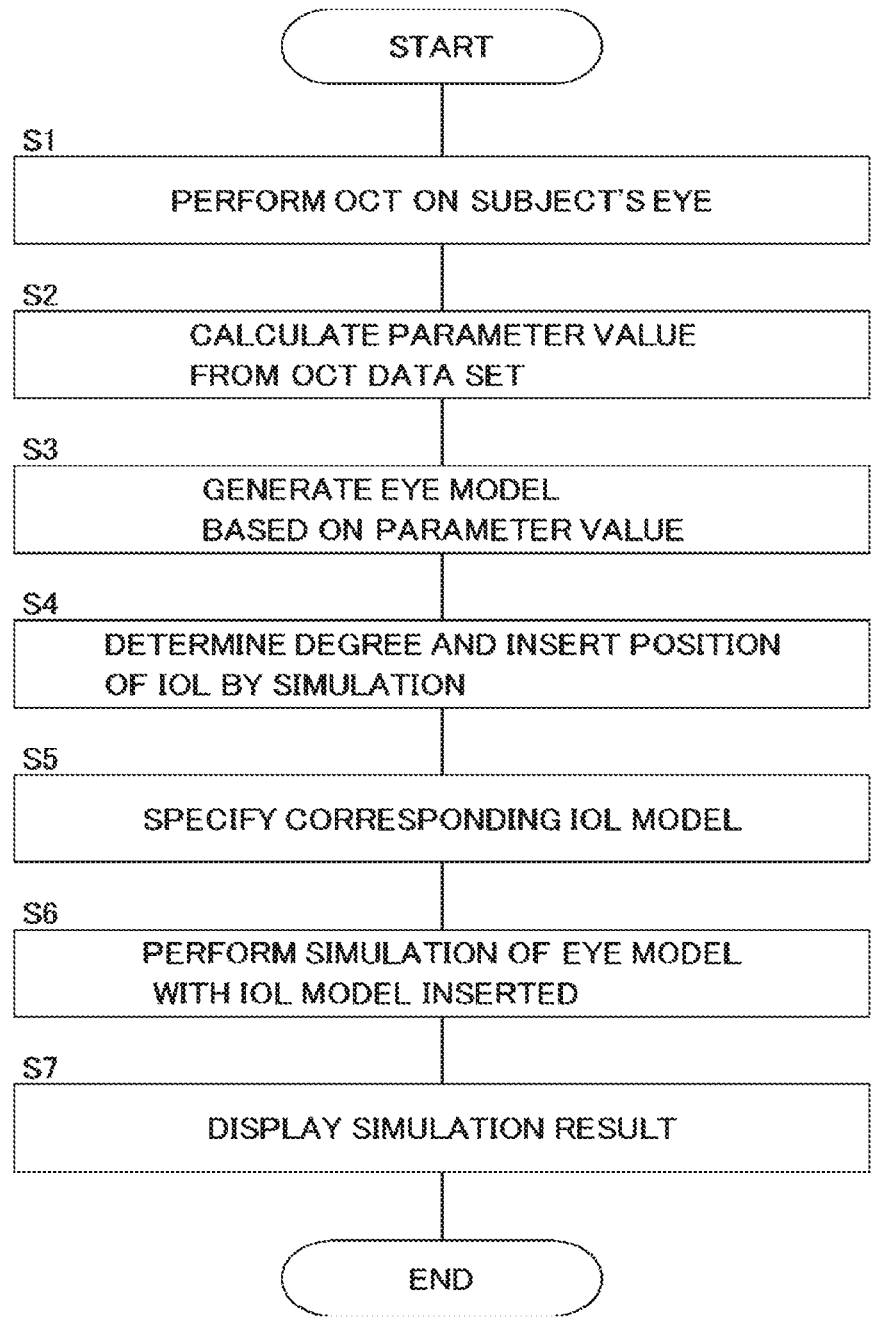
FIG. 5 is a flowchart illustrating an example of the operation of the ophthalmic imaging apparatus according to an embodiment.

The operation of the ophthalmic imaging apparatus 1 according to the embodiment will be described. An example of the operation of the ophthalmic imaging apparatus 1 is shown in FIG. 5.

(S1: Perform OCT on Subject's Eye)

First, the ophthalmic imaging apparatus 1 applies OCT to the subject's eye E to obtain a data set.

When a highly depth reachable light source is used as a light source for OCT, A lines extending at least from the anterior surface of the cornea to the retina are measured at a time. For example, when OCT is applied to the three-dimensional region R1 shown in FIG. 6A, OCT measurement is performed at a time for the A line represented by a line segment A1 that connects the +z side end and the −z side end of the three-dimensional region R1 and is parallel to the z direction.

Figure 6A:
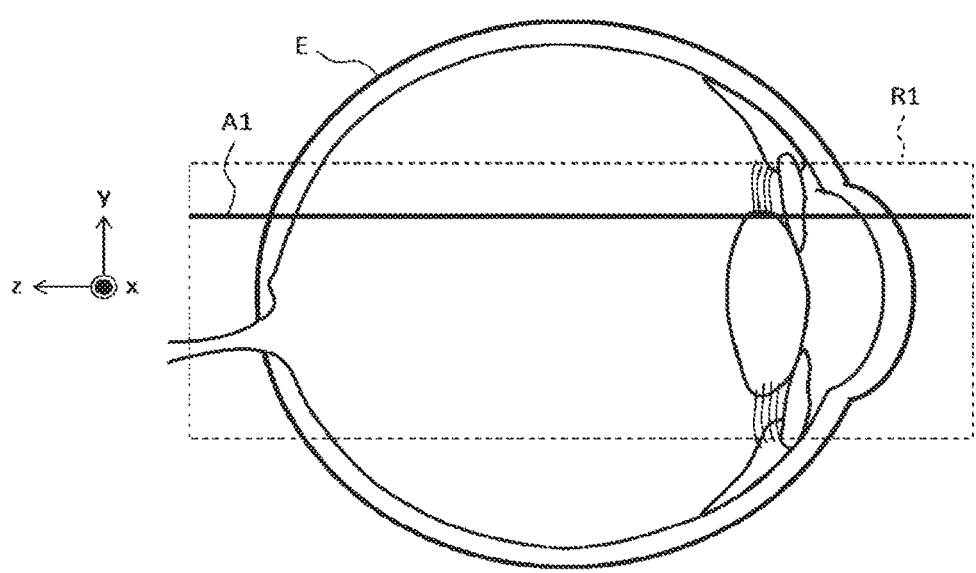
FIG. 6A is a schematic diagram for describing an operation of the ophthalmic imaging apparatus according to an embodiment.
Figure 6B:
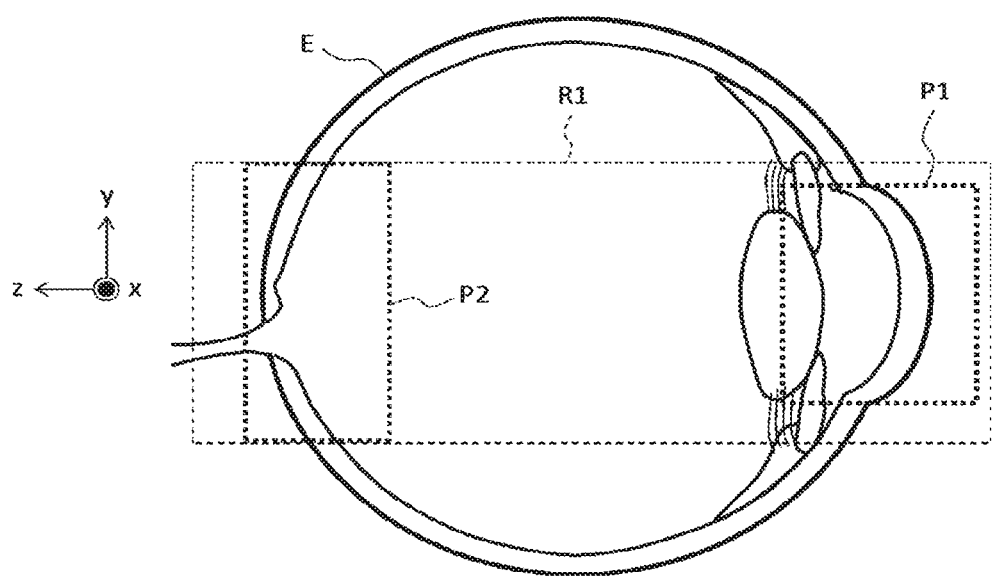
FIG. 6B is a schematic diagram for describing an operation of the ophthalmic imaging apparatus according to an embodiment.

In another case, it is possible to perform OCT on a partial region(s) between the front surface and the rear surface of a three-dimensional region using a highly depth reachable light source or using another light source. For example, as shown in FIG. 6B, OCT can be performed on two partial regions P1 and P2 in the same three-dimensional region R1 as shown in FIG. 6A. Here, the partial region P1 corresponds to the anterior segment (cornea, iris, crystalline lens, etc.), and the partial region P2 corresponds to the fundus Ef (retina, choroid, sclera etc., and vitreous body).

Figure 6C:
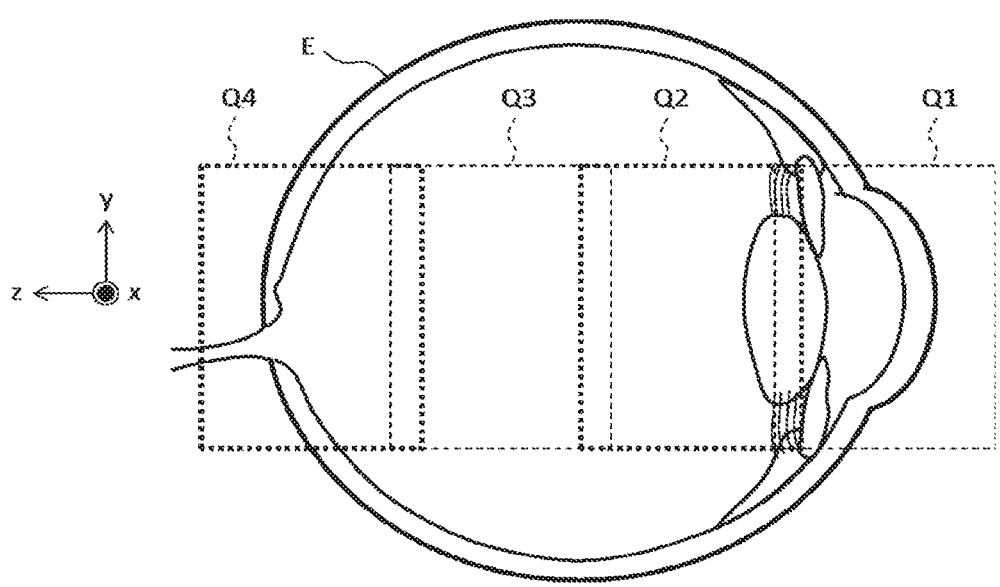
FIG. 6C is a schematic diagram for describing an operation of the ophthalmic imaging apparatus according to an embodiment.

Alternatively, when a highly depth reachable light source is not applied, it is possible to divide a three-dimensional region extending at least from the anterior surface of the cornea to the surface of the retina into two or more partial regions, and to perform OCT consecutively on the partial regions. For example, as shown in FIG. 6C, OCT can be consecutively performed on four partial regions Q1 to Q4 of the three-dimensional region extending at least from the anterior surface of the cornea to the surface of the retina. Note that adjacent partial regions Qi and Q (i+1) partially overlap each other (i=1, 2, 3). With this, it becomes easy to compose the four data sets (images) corresponding to the four partial regions Q1 to Q4.

(S2: Calculate Parameter Value from OCT Data Set)

The parameter calculation unit 2311 analyzes the data set acquired by the OCT in step S1 to obtain values of predetermined parameters of the subject's eye E. In the present example, at least the values of the axial length and of the curvature (radius of curvature) of the anterior surface of the cornea are obtained.

(S3: Generate Eye Model Based on Parameter Value)

The model generation unit 2312 generates a three-dimensional eye model of the subject's eye E based on the values of parameters calculated in step S2. The three-dimensional eye model includes an image (three-dimensional OCT image) represented by the OCT data set and the values of parameters calculated by the parameter calculation unit 2311. The three-dimensional eye model may include a measurement value and/or a standard value other than the values of parameters calculated in step S2.

(S4: Determine Degree and Insertion Position of IOL by Simulation)

The intraocular lens calculation unit 2321 executes a simulation (including ray tracing) based on the three-dimensional eye model generated in step S3, thereby obtaining degree and insertion position of an intraocular lens to be applied to the subject's eye E.

(S5: Specify Corresponding IOL Model)

From the database stored in the intraocular lens database storage unit 2121, the intraocular lens model specification unit 2322 specifies an intraocular lens model corresponding to the degree of the intraocular lens obtained in step S4.

(S6: Perform Simulation of Eye Model with IOL Model Inserted)

The eye model generation unit 231 inserts the intraocular lens model specified in step S5 into the three-dimensional eye model. That is, the eye model generation unit 231 replaces the crystalline lens in the three-dimensional eye model with the intraocular lens model. Here, the eye model generation unit 231 places the intraocular lens model at the insertion position obtained in step S4. Then, the simulation execution unit 232 executes a simulation (including ray tracing) using the three-dimensional eye model into which the intraocular lens model has been inserted. Thereby, the simulation execution unit 232 determines whether the intraocular lens model specified in step S5 is appropriate. Here, it is assumed that the intraocular lens model is determined to be appropriate. The processing to be executed in the case where it is determined that the intraocular lens model is inappropriate has been described above.

(S7: Display Simulation Result)

The display controller 2111 displays the result of the above simulation on the display unit 241. Hereinafter, some examples of display modes of the simulation result will be described. Typical examples of simulation result to be displayed include the degree of the intraocular lens, the insertion position of the intraocular lens, the retinal projection image of the virtual object, the trajectory of the virtual ray obtained by the above ray tracing, and the like. In addition, the simulation result may include the values of parameters calculated for the simulation. The function of displaying such a simulation result is called an annotation display function or the like. Annotation is a character string or an image representing information such as a site subjected to imaging, a measurement item, a measurement result, a comment, or the like. It should be noted that any two or more of the following display modes may be combined.
(First Display Mode)

The display controller 2111 controls the display unit 241 to display the result of the simulation executed by the simulation execution unit 232 and an OCT image of the subject's eye E formed based on the data set acquired by the OCT.

Note that the OCT data set is three-dimensional image data. By applying a rendering process, such as multi planar reconstruction (MPR), volume rendering, or the like, to the OCT data set, thereby displaying a desired two-dimensional cross-sectional image, pseudo three-dimensional image, or the like.

Further, the OCT image displayed may be an image representing only the three-dimensional region to which the OCT has been applied, or an image formed by complementing the three-dimensional region with schematic images or other photographed images.

Figure 7A:
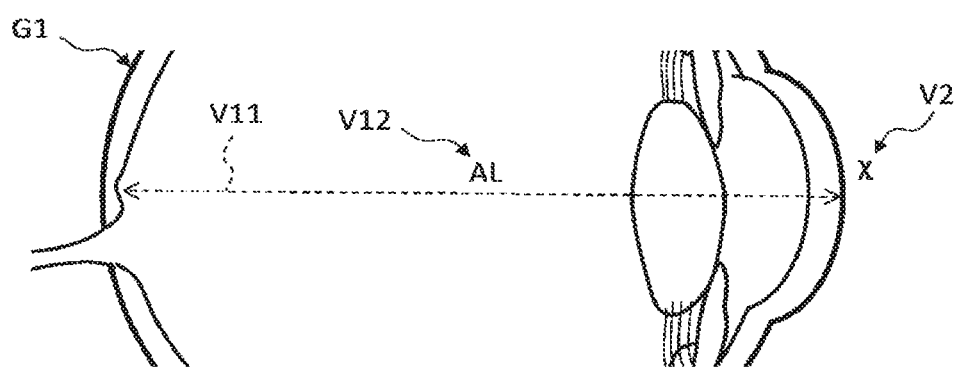
FIG. 7A is a schematic diagram for describing an operation of the ophthalmic imaging apparatus according to an embodiment.
Figure 7B:
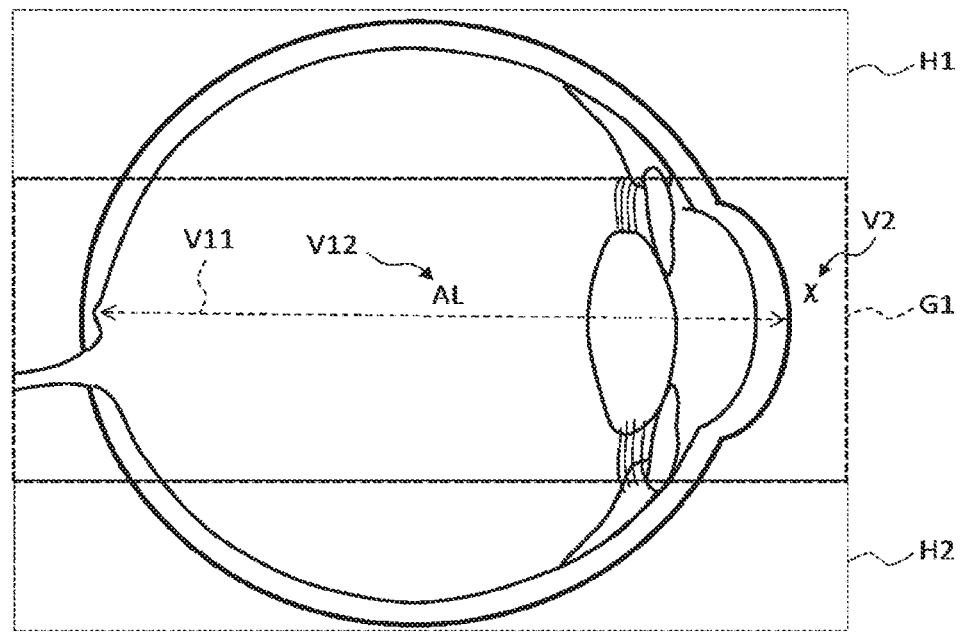
FIG. 7B is a schematic diagram for describing an operation of the ophthalmic imaging apparatus according to an embodiment.

Typical examples of the first display mode are shown in FIG. 7A and FIG. 7B. In the display example shown in FIG. 7A, a two-dimensional cross-sectional image G1 of the subject's eye E is displayed. The two-dimensional cross-sectional image G1 is an image representing only the three-dimensional region to which the OCT has been applied. Furthermore, an arrow image V11 representing the measurement position of the axial length are displayed on the two-dimensional cross-sectional image G1. In addition, the value "AL" V12 of the axial length calculated from the OCT data set is displayed on the two-dimensional cross-sectional image G1. Further, the value "χ" V2 of the curvature of the anterior surface of the cornea calculated from the OCT data set is displayed near the anterior surface of the cornea in the two-dimensional cross-sectional image G1.

In the display example shown in FIG. 7B, complementary images H1 and H2 for complementing the two-dimensional cross-sectional image G1 in FIG. 7A are displayed together with the two-dimensional cross-sectional image G1. Thus, the user can observe the entire image of the subject's eye E. Further, in the display example shown in FIG. 7B, as in FIG. 7A, the arrow image V11 representing the measurement position of the axial length, the axial length value "AL" V12 calculated from the OCT data set, and the curvature value "χ" V2 of the anterior surface of the cornea calculated from the OCT data set are displayed.
(Second Display Mode)

In the second display mode, the values of parameters calculated from the OCT data set, other measurement values and standard values can be selectively displayed.

The user designates one of the displayable parameters by operating the operation unit 242. The displayable parameters include, for example, one or more parameters associated with the three-dimensional eye model generated from the OCT data set. In this example, the displayable parameters are assumed to include the axial length and the curvature of the anterior surface of the cornea.

An example of processing for designating a parameter will be described. The display controller 2111 controls the display unit 241 to display a list of displayable parameters. This list may be, for example, a drop-down list in which displayable parameters are listed as options. Alternatively, this list may include options of displayable parameters and check boxes located near the respective options.

When at least one of the options of the parameters is designated, the display controller 2111 displays the designated value of the parameter together with the OCT image of the subject's eye E. When none of the options is designated, only the OCT image of the subject's eye E is displayed.

Figure 8A:
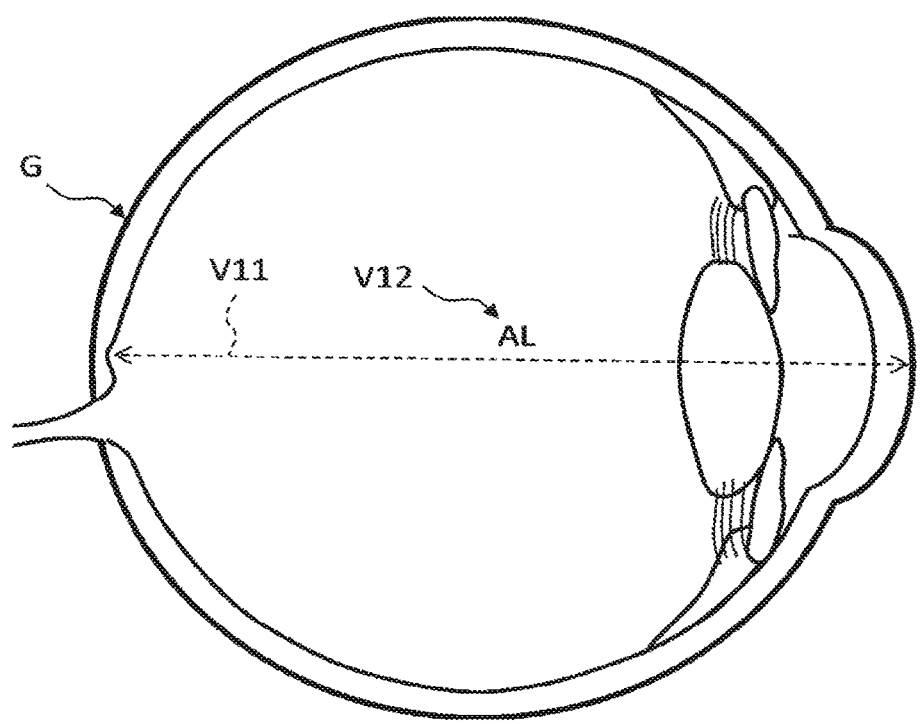
FIG. 8A is a schematic diagram for describing an operation of the ophthalmic imaging apparatus according to an embodiment.
Figure 8B:
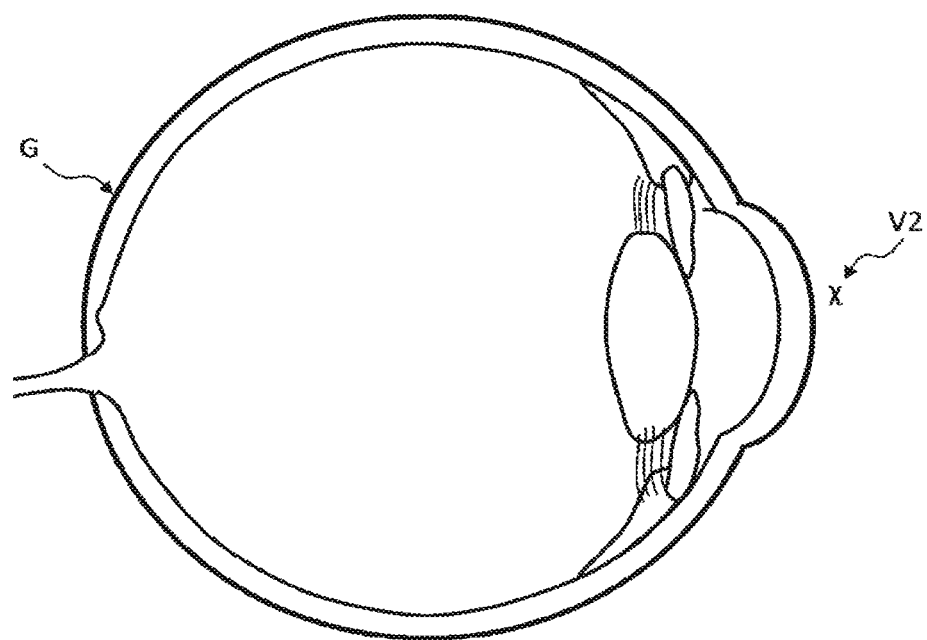
FIG. 8B is a schematic diagram for describing an operation of the ophthalmic imaging apparatus according to an embodiment.

FIG. 8A and FIG. 8B show typical examples of the second display mode. The display example shown in FIG. 8A illustrates a case in which only the axial length is designated from the displayable parameters. In this case, the display controller 2111 displays the arrow image V11 indicating the measurement position of the axial length and the axial length value "AL" V12 calculated from the OCT data set, together with the two-dimensional cross-sectional image G as in FIG. 7B.

The display example shown in FIG. 8B illustrates a case in which only the curvature of the anterior surface of the cornea is designated from the displayable parameters. In this case, the display controller 2111 displays the curvature value "χ" V2 of the anterior surface of the cornea, together with the two-dimensional cross-sectional image G as in FIG. 7B.
(Third Display Mode)

In the third display mode, an image of an intraocular lens can be displayed in addition to the OCT image and the values of parameters of the subject's eye E.

In the intraocular lens image storage unit 2122, image data representing an intraocular lens is stored in advance. The display controller 2111 acquires image data from the intraocular lens image storage unit 2122 and displays an intraocular lens image based on the acquired image data, together with the OCT image and the values of parameters of the subject's eye E.

In this process, the display controller 2111 may apply, to the image data acquired from the intraocular lens image storage unit 2122, the same rendering processing as that has been applied to from the OCT image. Then, the display controller 2111 can display an intraocular lens image representing the same cross section as that of the OCT image when the OCT image is a two-dimensional cross-sectional image. Alternatively, when the OCT image is a pseudo three-dimensional image, the display controller 2111 can display an intraocular lens image formed by applying the same sight line direction as that of the OCT image.

In another example, the display controller 2111 may be configured to acquire image data corresponding to the type of the intraocular lens specified by the simulation from the intraocular lens image storage unit 2122, and display an intraocular lens image based on the acquired image data.

Figure 9:
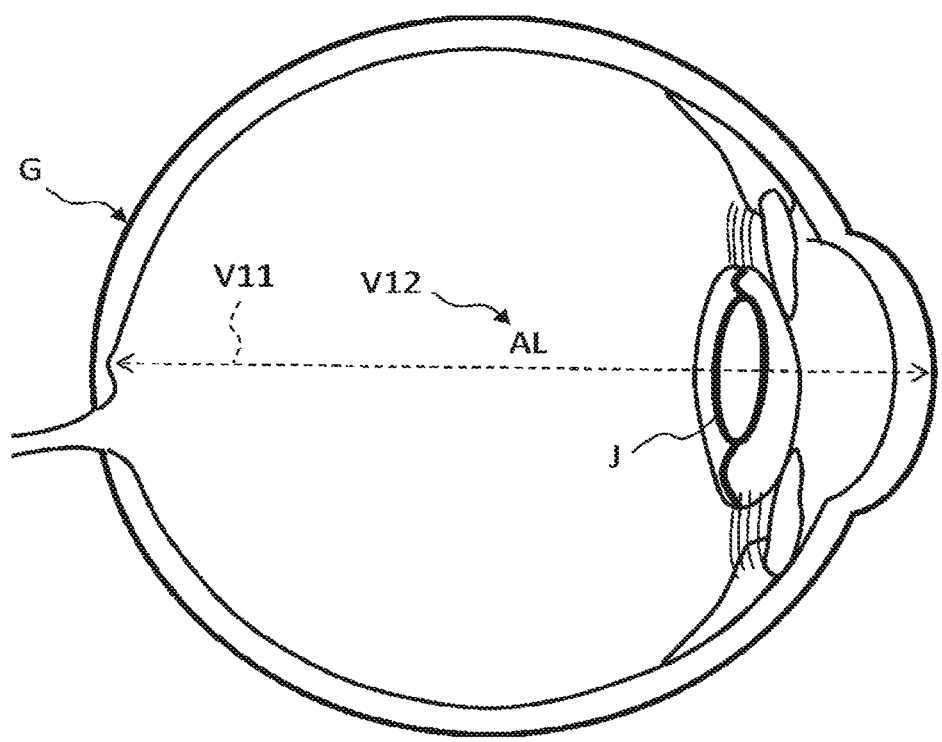
FIG. 9 is a schematic diagram for describing an operation of the ophthalmic imaging apparatus according to an embodiment.

In the display example shown in FIG. 9, an intraocular lens image J is displayed on the two-dimensional cross-sectional image G in addition to the followings: the two-dimensional cross-sectional image G as in FIG. 7B; the arrow image V11 indicating the measurement position of the axial length; the axial length value "AL" V12 calculated from the OCT data set; and the curvature value "χ" V2 of the anterior surface of the cornea. Here, the position at which the intraocular lens image J is displayed corresponds to the insertion position of the intraocular lens obtained in step S4.
(Fourth Display Mode)

The ophthalmic imaging apparatus 1 may be configured to be capable of changing the displayed annotation. For example, in response to the change in the position or length of the arrow image V11, which represents the measurement position of the axial length, by the use of the operation unit 242, the parameter calculation unit 2311 can calculate the value of the axial length based on the measurement position after the change. Further, the data processor 230 can generate a new eye model or re-execute the simulation based on the new value of parameter calculated in this manner.

As another example, the user can change the position and/or orientation of the intraocular lens image J, or to reselect an intraocular lens image. In response to such an operation, the data processor 230 can re-execute the simulation such as ray tracing.

[Effects]

The effects of the ophthalmic imaging apparatus 1 according to the embodiment will be described.

The ophthalmic imaging apparatus 1 according to the embodiment includes a measurement unit (the optical system for OCT, the image forming unit 220, the data processor 230, etc.), an eye model generation unit (231), and a simulation execution unit (232). The measurement unit is configured to acquire a data set by performing OCT on a three-dimensional region of the subject's eye including an area extending from the anterior surface of the cornea to the surface of the retina. The eye model generation unit is configured to analyze the data set acquired by the measurement unit to obtain values of one or more parameters of the subject's eye, and to generate a three-dimensional eye model based on the values acquired. The simulation execution unit is configured to execute a simulation based on the three-dimensional eye model generated by the eye model generation unit.

According to such an embodiment, an eye model with a higher reliability and accuracy than that obtained in the conventional manner can be obtained based on the data set obtained by the use of OCT with high resolution. In particular, since the embodiment is configured to obtain the data set by applying OCT to the three-dimensional region of the subject's eye including the area extending from the anterior surface of the cornea to the surface of the retina, the embodiment has the advantage of being capable of generating the three-dimensional eye model over the entire depth range of the subject's eye. By using such a three-dimensional eye model, an error included in the result of the simulation becomes smaller than that in the conventional one. The embodiment also has the advantage of giving the same effect even for a subject's eye with disease.

Further, the conventional technology can only obtain the values of parameters of the subject's eye and cannot obtain the structure of the subject's eye; however, the present embodiment can obtain both the values of parameters of the subject's eye and the structure of the subject's eye. In addition, since the embodiment is configured to obtain the values of parameters based on the OCT data set representing the structure of the subject's eye, it is advantageous in that there is no error between the values of parameters and the structure. As a result, it is possible to check whether the values of parameters correctly represent the characteristics of the subject's eye. For example, in axial length measurement, it is possible to check whether one end of the line segment representing the axial length is located at the apex of the cornea and the other end is located at the fovea centralis. Therefore, even when the measurement has been performed in a state in which the line of sight is deviated, the present embodiment can generate an eye model with an error caused by the measurement eliminated.

Furthermore, since the conventional technology generates an eye model based solely on the values of the parameters, the actual structure of the subject's eye cannot be visualized. In contrast, the present embodiment can visualize an image of the subject's eye using the data set obtained by OCT. Thereby, simulations using the eye model can be facilitated and labor saving can be achieved. Moreover, with the embodiment, even doctors without considerable experience can carry out simulations with relative ease.

As described above, the ophthalmic imaging apparatus 1 according to the embodiment is capable of easily acquiring eye models with high reliability, and of suitably executing simulations using the eye model.

In the embodiment, the parameters obtained from the data set acquired by the OCT may include at least one of the followings: a size parameter representing the size of part or whole of an eye; a shape parameter representing the shape of a site of the eye; and an optical parameter representing an optical function of a site of the eye. It is possible to arbitrarily select the types of parameters to be applied.

In the embodiment, the simulation execution unit is configured to be capable of executing ray tracing on light passing through the three-dimensional eye model of the subject's eye.

With such a configuration, simulations can be carried out with high reliability and high accuracy based on the behavior of rays in the three-dimensional eye model.

In the embodiment, the size parameter may include at least the axial length of the subject's eye, and the shape parameter may include the curvature of the anterior surface of the cornea of the subject's eye. In this case, the simulation execution unit may obtain the degree of and the insertion position of an intraocular lens by executing a simulation based on the three-dimensional eye model to which the value of the axial length of the subject's eye and the value of the curvature of the anterior surface of the cornea of the subject's eye are applied.

With such a configuration, it is possible to acquire the degree of an intraocular lens to be applied to the subject's eye, and to acquire the insertion position of the intraocular lens. The degree and the insertion position of the intraocular lens thus obtained are higher in reliability and higher in accuracy in comparison to those obtained using the conventional technology.

In the embodiment, the simulation execution unit is configured to be capable of executing ray tracing on light passing through the three-dimensional eye model in which a crystalline lens is replaced with the intraocular lens, based on the degree of and the insertion position of the intraocular lens obtained by the simulation.

With such a configuration, it is possible to determine the optical characteristics of the subject's eye after implantation of the intraocular lens (that is, after the subject's eye undergoes cataract operation). As a result, it is possible to determine whether or not the degree of and the insertion position of the intraocular lens to be applied are appropriate.

The embodiment may include a database storage unit (intraocular lens database storage unit 2121) in which a database including values of parameters with respect to a plurality of intraocular lens models is stored in advance. In this case, the simulation execution unit may include an intraocular lens model specification unit (2322) which specifies an intraocular lens model corresponding to the degree of the intraocular lens obtained by the simulation from among the plurality of intraocular lens models stored in the database. Further, the simulation execution unit may execute the ray tracing on the three-dimensional eye model in which the crystalline lens is replaced with the intraocular lens model specified by the intraocular lens model specification unit.

With such a configuration, for example, it is possible to determine the optical characteristics of the subject's eye when various existing intraocular lenses are implanted in the subject's eye. As a result, it is possible to determine whether or not the degrees of and the insertion positions of existing intraocular lenses to be applied are appropriate for the subject's eye. In addition, it is possible to select an existing intraocular lens suitable for the subject's eye.

The embodiment may include a display controller (2111) configured to display, on a display means (display unit 241), the result of the simulation executed by the simulation execution unit and an image of the subject's eye based on the data set acquired by the OCT.

With such a configuration, it is possible to visualize the actual structure of the subject's eye, and it is also possible to present the result of the simulation. In this manner, by presenting the structure of the subject's eye and the result of simulation together, the user is able to understand the state of the subject's eye in more detail. This contributes to ease of and labor saving of diagnosis, as well as rapidity of diagnosis, for example.

In the embodiment, the display controller may display the values of the parameters acquired by the eye model generation unit as the result of the simulation.

According to this configuration, it is possible to present useful diagnostic materials such as the size of part or the whole of the eye, the shape of the site of the eye, and the optical function of the site of the eye.

The embodiment may include an operation unit (242) used for designating any of the one or more parameters of the subject's eye. In this case, the display controller can selectively display the values of the one or more parameters based on the result of the designation of the parameters by the use of the operation unit.

With this configuration, it is possible to selectively present only necessary information. Further, there is an advantage that part (for example, region of interest) of the image of the subject's eye is not hidden by the displayed information (annotation).

Note that it is possible to configure so that the position of the annotation can be arbitrarily changed. Here, the operation unit may be used for changing the display position of the annotation, for example. Alternatively, it is also possible to adopt a configuration of displaying the annotation at a position different from that of the region of interest set in advance.

The embodiment may include an image data storage unit (intraocular lens image storage unit 2122) in which image data representing an intraocular lens is stored in advance. In this case, the display controller may display an intraocular lens image based on the image data representing the intraocular lens, together with the result of the simulation and the image of the subject's eye.

According to this configuration, it is possible to visualize the state of the subject's eye in which the intraocular lens is implanted. In particular, by displaying the intraocular lens image at the insertion position obtained by simulation, the user is able to understand the state of the subject's eye in which the intraocular lens is implanted in detail.

The measurement unit may include an optical system configured to perform OCT with light (first light) output from a highly depth reachable light source. Further, the measurement unit may include an image data generation unit (the image forming unit 220, the data processor 230, etc.) configured to perform the following processes: acquisition of a plurality of reflection intensity profiles extending from the front surface to the rear surface of the three-dimensional region including the area extending from the anterior surface of the cornea to the surface of the retina based on the result of detection obtained by the optical system; and generation of image data of the three-dimensional region based on the plurality of reflection intensity profiles acquired.

With such a configuration, the OCT on the three-dimensional region including the area extending from the anterior surface of the cornea to the surface of the retina can be executed at a time without changing the measurement depth. As a result, it is possible to shorten the time taken for OCT.

In the embodiment, the optical system may be configured to perform OCT using second light output from a light source. In this case, the image data generation unit may generate image data of a partial region between the front surface and the rare surface of the three-dimensional region including the area extending from the anterior surface of the cornea to the surface of the retina.

According to this configuration, in addition to the effect that OCT can be performed for a wide depth range at a time using a high depth reachable light source, a high-resolution image can be acquired for a site of the eye, like the region of interest, requiring a high-resolution image.

In the embodiment, the measurement unit may be configured to acquire a group of data sets by consecutively applying OCT to two or more partial regions of the three-dimensional region, in which union of the two or more partial regions is the three-dimensional region including the area extending from the anterior surface of the cornea to the surface of the retina. That is, the measurement unit can execute OCT on the three-dimensional region including the area extending from the anterior surface of the cornea to the surface of the retina, for the partial regions thereof in a consecutive manner. Furthermore, the eye model generation unit may be configured to generate the three-dimensional eye model based on the group of data sets acquired by such a series of OCT.

According to this configuration, the processing according to this embodiment can be implemented by the use of a light source commonly and widely used at present without having to use a highly depth reachable light source.

Second Embodiment

Reference will be made appropriately to the drawings according to the first embodiment. Unless otherwise mentioned, description will include the same reference symbols for the same elements as those of the first embodiment. In addition, arbitrary items described in the first embodiment can be applied to the second embodiment.

In the second embodiment, a time-dependent image is acquired by OCT. The time-dependent image includes a plurality of OCT images (a plurality of data sets) which are ordered in time series. In other words, the time-dependent image includes a plurality of OCT images acquired at different timings from one another. An example of the time-dependent image is a moving image composed of a plurality of still images (image frames) acquired at a fixed time interval (i.e., at a fixed frame rate). It should be noted that the acquisition intervals of a plurality of still images does not need to be constant.

Such an OCT moving image can be obtained by repeatedly executing scanning with the same pattern. The repetition rate of the scanning corresponds to the frame rate. When image integration for improving image quality of each image frame is executed, a value obtained by dividing the repetition rate of scanning by the number of image frames integrated together becomes the frame rate. In addition, the scanning pattern is a three-dimensional scanning, and its target region is a three-dimensional region including an area extending from the anterior surface of the cornea to the surface of the retina. According to the OCT moving image acquired by such a scanning, it is possible to perceive the time-dependent change of the three-dimensional region including the area extending from the anterior surface of the cornea to the surface of the retina.

The parameter calculation unit 2311 of the eye model generation unit 231 calculates values of predetermined parameters for each image frame by analyzing each image frame acquired by the repetition of the three-dimensional scanning performed in the above described manner. The processing executed for each image frame may be the same as that in the first embodiment. According to this processing, a time-dependent changes in the values of the predetermined parameters can be obtained.

Subsequently, the model generation unit 2312 generates a three-dimensional eye model based on the values of parameters obtained for each image frame. Information representing acquisition timing of the corresponding image frame is assigned to each three-dimensional eye model generated. The acquisition timing information may be, for example, information representing the time at which the image frame has been acquired, information representing the order of the image frames (i.e., information indicating the sheet number of the corresponding image frame), or the like. Through such processing, a plurality of three-dimensional eye models is obtained with which acquisition timing information indicating different times or numbers are associated. In other words, a three-dimensional eye model that changes with time (i.e., four-dimensional eye model) can be obtained.

If the subject's eye E moves while the OCT is being executed, the three-dimensional region depicted in the image frames shifts. In many cases, the shift of the depicted region is very small. It is possible to solve such a shift and perform moving image display. A typical example of such processing includes: the followings: processing for specifying a feature point in each image frame; processing for calculating the displacement of the feature point in one frame with respect to the position of the feature point in another frame; and processing for adjusting the positions (i.e., registration) of the plurality of frames so as to eliminate the displacements calculated. In another example, the processing may include the followings: processing for specifying a feature point in each image frame; processing for consecutively calculating displacements of the feature points between consecutive image frames; and processing for consecutively adjusting the positions of the plurality of image frames so as to eliminate the cumulative displacements of the feature points calculated by the previous processing.

Based on the plurality of image frames acquired by the repetition of the three-dimensional scanning as described above (or, based on a four-dimensional eye model based on the image frames), the eye model generation unit 231 acquires information representing time-dependent change (time-dependent change information) of a target inside the subject's eye. The target may be a site of the subject's eye E (for example, the crystalline lens, the Zinn's zonule, the ciliary muscle, etc.), a body fluid existing inside the subject's eye E, a member inserted in the subject's eye E (an intraocular lens, etc.), or a medicine administered to the subject's eye E. An example of the medicine is a medicine administered in the vitreous body for the treatment of age-related macular degeneration. By such processing, the eye model generation unit 231 acquires motion information representing the motion of a site of the subject's eye, distribution change information representing the change in distribution of liquid inside the subject's eye, or the like. Here, the distribution change information may include the change in the region in which the liquid exists, or the change in the concentration of the liquid at each position.

The processing for acquiring the time-dependent change information is executed as follows, for example. First, the eye model generation unit 231 analyzes each of a plurality of image frames (or a plurality of three-dimensional eye models) to specify image areas in the image frames corresponding to the target. Next, the eye model generation unit 231 determines time-dependent changes in the morphology (position, orientation, size, etc.) of the target based on the plurality of image areas specified from the plurality of image frames.

The effects of the ophthalmic imaging apparatus according to the second embodiment will be described.

The ophthalmic imaging apparatus according to the present embodiment includes a measurement unit (the optical system for OCT, the image forming unit 220, the data processor 230, etc.), an eye model generation unit (231), and a simulation execution unit (232). The measurement unit is configured to acquire a plurality of data sets (a plurality of OCT images, a plurality of image frames) in chronological order by iteratively applying OCT to the three-dimensional region including the area extending from the anterior surface of the cornea to the surface of the retina of the subject's eye. The eye model generation unit is configured to acquire values of parameters of the subject's eye by analyzing each of the plurality of data sets acquired by the measurement unit, and to generate a three-dimensional eye model which changes with time based on the values of the parameters acquired. The simulation execution unit executes a simulation based on the three-dimensional eye model which changes with time generated by the eye model generation unit.

According to such an embodiment, as in the first embodiment, it is possible to easily acquire an eye model with high reliability and suitably execute simulation. In addition, according to this embodiment, it is possible to execute not only the simulation of a static morphology of the subject's eye, but also a dynamic simulation of the subject's eye.

In the embodiment, the ophthalmic imaging apparatus obtains information representing time-dependent change of a target inside a subject's eye based on the plurality of data sets acquired by the measurement unit.

According to this configuration, it is possible to acquire motion information representing the motion of a site of the subject's eye (the crystalline lens, the Zinn's zonule, the ciliary muscle, or the like) or distribution change information representing the change in distribution of liquid (medicine etc.) inside the subject's eye. The information obtained in this way can be used for simulations. It is also possible to use the information obtained in this way as a diagnostic material together with the results of the simulation.

<Ophthalmic Information Processing Apparatus>

The present invention also includes an apparatus configured to execute processing similar to that of the first or second embodiment based on a data set(s) acquired by an external device. Typical examples of such apparatuses are computers, mobile terminals (tablets, smart phones, etc.), servers on a LAN, servers on a WAN, ophthalmic apparatuses without the OCT function, ophthalmic apparatuses with the OCT function, medical apparatuses that can be used in the field other than the field of ophthalmology, and the like.

An ophthalmic information processing apparatus of an embodiment includes a reception unit, an eye model generation unit, and a simulation execution unit. The reception unit is configured to receive a data set acquired by applying OCT to a three-dimensional region of a subject's eye including an area extending from an anterior surface of a cornea to a surface of a retina. The reception unit receives the data set via, for example, a network or a recording medium. A reception unit for receiving a data set via a network includes a network adapter (a LAN card, a modem, etc.). A reception unit for receiving a data set via a recording medium includes a drive device for the recording medium. or an external bus. The eye model generation unit is configured to acquire values of one or more parameters of the subject's eye by analyzing the data set received by the reception unit, and to generate a three-dimensional eye model based on the values of parameters acquired. The processing executed by the eye model generation unit may be the same as that in the first or second embodiment. The simulation execution unit is configured to execute a simulation based on the three-dimensional eye model generated by the eye model generation unit. The processing executed by the simulation execution unit may be the same as that in the first or second embodiment.

According to such an ophthalmic information processing apparatus, it is possible to easily acquire an eye model with high reliability based on the OCT data set acquired by the external device, and suitably execute simulation by the use of the eye model.

The ophthalmic information processing apparatus according to the embodiment may have any configuration described in the first or second embodiment.

Other Embodiments

In the above embodiments, a case of executing simulation of a crystalline lens (intraocular lens) has been specifically described in detail; however, a target of simulation is not limited to crystalline lenses. As a specific example, simulation of a cornea can be executed. With this, it is possible to acquire information for corneal refractive correction.

For example, with respect to LASIK, a typical example of corneal refractive surgery, it is possible to execute simulation for determining the position of a flap and for determining transpiration position and transpiration volume. Further, similar simulations can be executed for PRK, LASEK and Epi-LASIK.

It is also possible to execute simulations to prescribe contact lenses.

A computer program for implementing the above embodiment or its modified example can be stored in any recording medium readable by a computer. Examples of the recording medium that can be used include a semiconductor memory, an optical disk, a magneto-optical disk (CD-ROM/DVD-RAM/DVD-ROM/MO, etc.), a magnetic storage medium (hard disk/floppy (registered trademark) disk/ZIP, etc.), and the like. It is also possible to send and receive the program via a network such as the Internet or LAN.

The configurations described above are mere examples for embodying or carrying out the present invention, and therefore susceptible to several modifications and variations (omission, substitution, addition, etc.), all coming within the scope of the invention.

What is claimed is:
1. An ophthalmic imaging apparatus comprising:
   a measurement unit configured to acquire a data set by applying optical coherence tomography to a three-dimensional region of a subject's eye including an area extending from an anterior surface of a cornea to a surface of a retina;
   an eye model generation unit configured to acquire values of one or more parameters of the subject's eye by analyzing the data set acquired by the measurement unit, and to generate a three-dimensional eye model based on the values acquired; and
   a simulation execution unit configured to execute a simulation based on the three-dimensional eye model generated by the eye model generation unit;
   wherein the measurement unit comprises:
   an optical system configured to split first light output from a highly depth reachable light source into measurement light and reference light, and to detect interference light generated by superposing the measurement light returning from the subject's eye on the reference light; and
   an image data generation unit configured to acquire a plurality of reflection intensity profiles extending from a front surface to a rear surface of the three-dimensional region based on a result of detection of the interference light by the optical system, and to generate image data of the three-dimensional region as the data set based on the plurality of reflection intensity profiles acquired.
2. The ophthalmic imaging apparatus of claim 1, wherein
   the optical system is configured to split second light output from a light source into measurement light and reference light, and to detect interference light generated by superposing this measurement light returning from the subject's eye on this reference light, and
   the image data generation unit is configured to generate image data of a partial region between the front surface and the rare surface of the three-dimensional region.

* * * * *

UNITED STATES PATENT AND TRADEMARK OFFICE
CERTIFICATE OF CORRECTION

| | | |
|---|---|---|
| PATENT NO. | : 10,105,052 B2 | Page 1 of 1 |
| APPLICATION NO. | : 15/509384 | |
| DATED | : October 23, 2018 | |
| INVENTOR(S) | : Takaichi Tamura | |

It is certified that error appears in the above-identified patent and that said Letters Patent is hereby corrected as shown below:

On the Title Page

Item (73), the Assignee's information is incorrect. Item (73) should read:
--(73) Assignee: KABUSHIKI KAISHA TOPCON, Itabashi-ku (JP)--

Signed and Sealed this
Sixth Day of August, 2019

Andrei Iancu
*Director of the United States Patent and Trademark Office*